United States Patent [19]

DeGregoria et al.

[11] Patent Number: 5,617,913
[45] Date of Patent: Apr. 8, 1997

[54] ELASTOMER BED FOR HEATING AND MOISTURIZING RESPIRATORY GASES

[75] Inventors: Anthony J. DeGregoria; Thomas J. Kaminski, both of Madison, Wis.

[73] Assignee: ElasTek, Inc., Madison, Wis.

[21] Appl. No.: 439,430

[22] Filed: May 11, 1995

Related U.S. Application Data

[60] Continuation-in-part of Ser. No. 226,479, Apr. 12, 1994, Pat. No. 5,465,781, which is a division of Ser. No. 968,341, Oct. 29, 1992, Pat. No. 5,339,653.

[51] Int. Cl.$^6$ .................................................. F28D 15/00
[52] U.S. Cl. ............................. 165/104.11; 128/201.13; 128/204.17; 165/4
[58] Field of Search ............................. 165/4, 6, 104.11; 128/201.13, 204.17, 205.27

[56] References Cited

U.S. PATENT DOCUMENTS

| | | |
|---|---|---|
| Re. 26,560 | 4/1969 | Meredith . |
| 2,610,038 | 9/1952 | Phillips ............................. 128/201.13 |
| 2,931,189 | 4/1960 | Sigworth ................................. 62/172 |
| 3,036,444 | 5/1962 | Cochran .................................. 62/467 |
| 3,099,987 | 8/1963 | Bartlett, Jr. ........................ 128/201.13 |
| 3,326,214 | 6/1967 | McCoy ............................... 128/201.13 |
| 3,333,585 | 8/1967 | Barghini et al. ................... 128/201.13 |
| 3,599,443 | 8/1971 | Paine ....................................... 62/467 |
| 3,747,598 | 7/1973 | Cowans ............................. 128/201.13 |
| 3,814,094 | 6/1974 | De Angelis et al. .............. 128/201.13 |
| 3,920,009 | 11/1975 | Olsen ................................. 128/201.13 |
| 4,054,980 | 10/1977 | Roma ................................... 165/172 X |
| 4,069,028 | 1/1978 | Brown ....................................... 62/3 |
| 4,124,478 | 11/1978 | Tsien et al. .......................... 165/166 X |
| 4,201,206 | 5/1980 | Kuehn et al. ...................... 128/201.13 |
| 4,258,784 | 3/1981 | Perry et al. ............................. 165/166 |
| 4,294,242 | 10/1981 | Cowans ............................. 128/201.13 |
| 4,325,365 | 4/1982 | Barbuto ............................. 128/201.13 |
| 4,327,717 | 5/1982 | Oetjen et al. ...................... 128/201.13 |
| 4,332,135 | 6/1982 | Barclay et al. .............................. 62/3 |
| 4,355,636 | 10/1982 | Oetjen et al. ...................... 128/204.13 |
| 4,411,310 | 10/1983 | Perry et al. ............................. 165/166 |
| 4,432,409 | 2/1984 | Steele ......................................... 165/8 |
| 4,512,392 | 4/1985 | van Ee et al. ............................ 165/54 |
| 4,574,872 | 3/1986 | Yano et al. ................................. 165/8 |
| 4,577,678 | 3/1986 | Franenfeld et al. ...................... 165/10 |
| 4,594,860 | 6/1986 | Coeliner et al. ..................... 165/10 X |
| 4,620,537 | 11/1986 | Brown ............................... 128/201.13 |

(List continued on next page.)

FOREIGN PATENT DOCUMENTS

| | | | |
|---|---|---|---|
| 0205072 | 12/1986 | European Pat. Off. .......... | 128/204.17 |
| 1234531 | 3/1965 | Germany . | |
| 3143088 | 10/1981 | Germany . | |
| 1360064 | 7/1974 | United Kingdom . | |
| 2082921 | 8/1980 | United Kingdom . | |
| 8904684 | 6/1989 | WIPO .............................. | 128/204.17 |

OTHER PUBLICATIONS

Pall Biomedical Inc., Heat and Moisture Exchanger for general adult anesthesia, Oct. 11, 1988.
*Cryogenics*, Pratt et al., vol. 17 (1977) pp. 689–693.
*J. Appl. Phys.*, Brown, vol. 47 (1976) pp. 3673–3680.
*Adv. Cryogenic Eng.*, A. J. DeGregoria et al., vol. 37, part B, (1992) pp. 875–882.
*The Physics of Rubber Elasticity*, Treloar, Oxford University Press (1958) pp. 38–43.
*The Engström Edith Humidification Handbook*, gambro engström, date unknown, pp. 1–30.

*Primary Examiner*—John Rivell
*Assistant Examiner*—Christopher Atkinson
*Attorney, Agent, or Firm*—Teresa J. Welch; Stroud, Stroud, Willink, Thompson & Howard

[57] ABSTRACT

A high performance, low cost, regenerator/heat enthalpy exchanger matrix or bed. The bed consist of a matrix of tensioned sheets with flow channels therethrough. The matrix is of the parallel plate type with high porosity, and narrow, uniform, unobstructed channels. The bed is ideal for near room temperature regenerator applications. The elastomer bed regenerative heat transfer structures are suitably used in heat and moisture exchangers which are used on humans to reduce moisture and heat loss during breathing.

35 Claims, 17 Drawing Sheets

U.S. PATENT DOCUMENTS

| | | | |
|---|---|---|---|
| 4,705,097 | 11/1987 | Mita et al. | 165/4 |
| 4,733,718 | 3/1988 | Schikowsky et al. | 165/4 |
| 4,744,414 | 5/1988 | Schon | 165/167 |
| 4,771,770 | 9/1988 | Artemenko et al. | 128/201.13 |
| 4,817,708 | 4/1989 | Ono et al. | 165/54 |
| 4,825,863 | 5/1989 | Dittmar et al. | 128/203.27 |
| 4,858,685 | 8/1989 | Szücs et al. | 165/166 |
| 4,875,520 | 10/1989 | Steele et al. | 165/10 |
| 4,955,435 | 9/1990 | Shuster et al. | 165/170 |
| 5,007,114 | 4/1991 | Numano | 128/201.13 X |
| 5,010,594 | 4/1991 | Suzuki et al. | 128/201.13 |
| 5,033,537 | 7/1991 | Atkin et al. | 165/32 |
| 5,035,236 | 7/1991 | Kanegaonkar | 128/201.13 |
| 5,035,240 | 7/1991 | Braun et al. | 128/205.27 |
| 5,320,096 | 6/1994 | Hans | 128/205.29 |
| 5,383,447 | 1/1995 | Lang | 128/201.13 |
| 5,435,298 | 7/1995 | Anthony | 128/204.17 X |

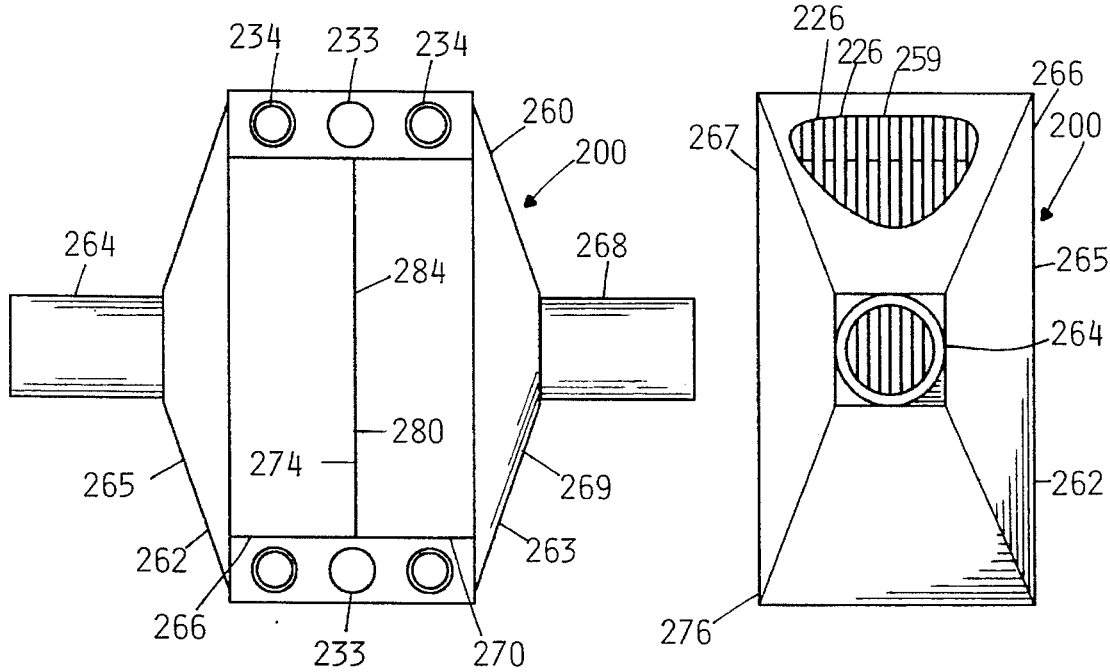
FIG. 7
FIG. 8
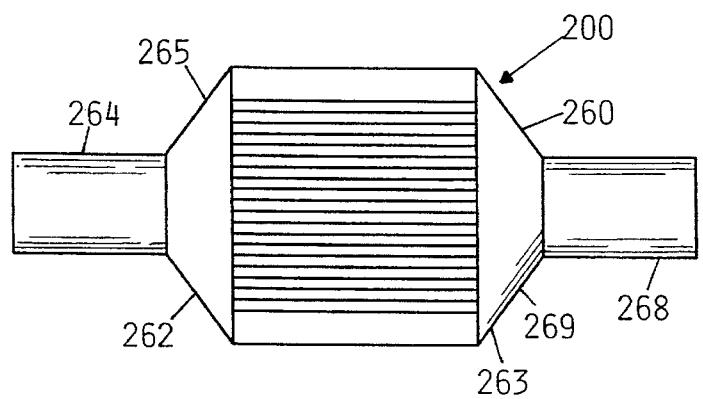
FIG. 6

ELASTOMER BED FOR HEATING AND MOISTURIZING RESPIRATORY GASES

This is a continuation-in-part of application Ser. No. 08/226,479, filed Apr. 12, 1994 now U.S. Pat. No. 5,465,781, that is a divisional of application Ser. No. 07/968,341 filed on Oct. 29, 1992 now issued as U.S. Pat. No. 5,339,653, on Aug. 23, 1994, the disclosures of which are incorporated herein by reference.

TECHNICAL FIELD

This invention relates generally to heat transfer devices, e.g., heat exchangers, enthalpy exchangers, heat and moisture exchangers, and, more specifically, to devices for heating and moisturizing respiratory gases during medical artificial ventilation and, utilizing the regenerator principle. The invention is particularly well-suited for near-room-temperature regenerator applications.

BACKGROUND OF THE INVENTION

Heat transfer devices, specifically heat exchangers, find all kinds of application from industrial operations to medical ventilation techniques. Simple heat exchangers transfer heat from an outgoing hot fluid to an incoming cool fluid. More recently, heat exchangers have utilized the regenerator principle.

The regenerator principle involves heat recovery when a fluid (referred to as a "shuttle fluid") is reciprocally exchanged between two reservoirs of different temperature, i.e., alternating flow by a hotter or colder fluid with some mechanism for effecting this reciprocating fluid flow through the system. The two-part regenerator cycle consists of flow of the fluid from the cold to the hot reservoir through a regenerator bed (or matrix) of porous heat transfer material, followed by flow of the fluid from the hot to the cold reservoir through the bed.

Where the heat capacity of the bed is very large compared to the heat capacity of the shuttle fluid, a temperature profile is established in the regenerator bed. The shuttle fluid is the total fluid mass that flows in one direction prior to reversal. After many reciprocating flows, the bed material establishes a temperature profile that increases from the side at which the cold fluid enters to the side at which the hot fluid enters. During the flow from cold to hot, the fluid enters at temperature $T_C$, the temperature of the cold heat exchanger. It is warmed by the bed as it passes through the bed, and leaves the bed at a temperature below $T_H$, the temperature of the hot exchanger. During flow from hot to cold, the fluid enters the bed at temperature $T_H$. It is cooled by the bed as it passes through and leaves the bed at a temperature above $T_C$. This difference in temperature of the fluid from entrance to exit from the bed, $\Delta T$, causes heat flow from the hot to cold reservoir. At worst, it is $T_H - T_C$, if there were no regenerator present. The ratio of $\Delta T$ to $(T_H - T_C)$ is referred to as the regenerator ineffectiveness. Over the cycle, the bed receives no net heat. It acts as an intermediate heat reservoir, absorbing heat from the warm gas and rejecting it to the cool gas.

Regenerative air-to-air heat exchangers are known; see, e.g., U.S. Pat. No. 4,875,520 issued to Steele et al. In such regenerators, it is important for the bed to have high heat capacity.

In other types of heat exchangers, two fluid streams are separated by the bed and flow continuously; here the heat capacity of the bed is irrelevant. See, for example, U.S. Pat. No. 4,858,685 issued to Szücs et al. It is important, however, in these cases, for the bed to have excellent thermal conductivity as well as high moisture transfer (when moisture retention is desirable).

Other known heat exchangers include U.S. Pat. No. 4,744,414 issued to Schon (continuous heat exchanger); U.S. Pat. No. 4,574,872 issued Yano et al. U.S. Pat. No. 4,574,872 (regenerative rotary type total heat exchanger); U.S. Pat. No. 4,577,678 issued to Franenfeld et al. (plastic storage material for heat transfer).

Another type of heat exchanger is an evaporative cooler which is disclosed in, e.g., U.S. Pat. No. Reissue 26,560 issued to Meredith. In the Meredith device, there is continuous flow of the liquid and gas, the two fluids. Air is forced through a matrix where the evaporating water cools and the air is, in turn, cooled in the matrix. A desirable matrix has high moisture absorption; thermal conduction and heat capacity are irrelevant. Meredith discloses a matrix using sheeting, fabric or filaments placed under tension. The liquid adheres to the fabric (matrix) as it flows downward. The fabric (matrix) performs no thermal function, and the liquid and gas are in direct contact. No heat is transferred to or through the fabric.

Moreover, a device such as that disclosed by Meredith is quite complex and uses plumbing and sprayers, for the water must flow down the fabric sheets or filaments while air flows between them. The layers must have separation significantly greater than the size of a water drop, "⅜ inch, more or less." The flow of air is turbulent, and Meredith describes the problem of "flutter" caused by angular rotation of a long, narrow strip of fabric in a fast moving turbulent air stream.

A specialized application of heat exchangers is in pulmonary medical devices for artificial ventilation. When human patients are on anesthesia machines during surgery or respirators during long-term pulmonary care, a ventilator is used to perform breathing for the patient. The ventilator forces air into the lungs via an endotracheal tube inserted into the trachea, then allows the lungs to exhale due to their compliance. This artificial ventilation is distinguished from normal breathing because the patient's nose is bypassed for breathing. As a consequence, the heating and moisturizing function of the nose is circumvented. It is well known that the cold, dry air impinging on a patient's respiratory airways, i.e., the trachea and the bronchial tubes, damages the lining of the airways over time.

Deep in the lungs, the measured state of air is 37° C. and 100% relative humidity, corresponding to an absolute moisture content of 44 mg of water per liter of air. Dry medical gases used for patient ventilation have temperatures at about 20° C. and a relative humidity (RH) of 0%, corresponding to an absolute moisture content of 0 mg/L of air. A perfect regenerative heat exchanger which transmits sensible heat only will reduce the temperature of the exhaled air to 20° C. Sensible heat is that portion of total heat content of air which can be sensed by a thermometer. Saturated air at 20° C. corresponds to an absolute moisture content of about 16 mg/L of air. Thus, in reducing the temperature of air to 20° C., 44mg/L minus 16 mg/L of moisture must be removed from the exhaled air. This moisture removal is achieved by condensing a thin film of moisture on the surface of the heat exchanger bed. In the case of exhalation, the patient will lose 16 mg of water per L of air exhaled and 28 mg of water per L of air (44 minus 16) will be condensed on the surface of the bed. On inhalation, the dry air will evaporate this thin film of water and the bed will warm the air to 37° C. Thus, the inhaled air will contain 28 mg absolute moisture per L of air.

Active heaters and moisturizers, typically, are used to provide warm moist air to the patient. Heated water humidifiers are used to insert moisture and heat into the incoming air flowing into the endotracheal tube. These devices and methods pose many problems. Electric heaters are used to evaporate the water, which must be sterile distilled water; the devices thus require monitoring and refilling. The devices also represent a potential shock and burn hazard to the patient and to those assisting in the patient's care. In addition to these problems, the exhaled air frown the patient has a dew point well above the temperature of the tubes which receive the exhaled air. Thus, condensation occurs in these tubes. Water traps are typically used to collect the condensation. The water traps also must be monitored and emptied on a regular basis. This condensation water can also be a biohazard. Thus, the active heat/moisture devices are expensive to operate and maintain, and pose significant patient risk.

Passive heat and moisture exchangers (HMEs) are also used. Like the active heaters and moisturizers, the primary function of an HME is to prevent patient moisture loss from the linings of the trachea and lungs.

For patient use in medical artificial ventilation, the HME devices are typically enclosed in a housing and are positioned in-line between the endotracheal tube and the Y-connector line to the ventilator, i.e., the patient breathes through the HME.

As explained hereinbefore, a heat and moisture exchanger should be able to absorb and desorb as much as 44 mg of water per L of air. Theoretically, an HME can return almost all of the exhaled moisture from the breath. Yet, even the best, currently available, return only about two-thirds of the maximum 44 mg of water per L. Return of the maximum amount of moisture is possible if hygroscopic materials are incorporated into the exchanger. With a hygroscopic material, water can be absorbed and desorbed at moisture levels below 100% relative humidity.

HMEs have been used for respiratory air heating both nonmedically and medically. A recent example of nonmedical use is SOUTHWIND™ RESPIRATOR, available from CenTex, Carbondale, Pa., Part No. WW-10. Nonmedical humidifying and air warming masks for a variety of bed materials include, for example, U.S. Pat. No. 3,814,094 to DeAngelis et al. (use of stacks of aluminum screening); U.S. Pat. No. 4,294,242 to Cowans (stainless steel screening); U.S. Pat. No. 5,010,594 to Suzuki et al. and U.S. Pat. No. 5,007,114 to Numano (bast paper fibers); U.S. Pat. No. 4,325,365 to Barbuto (spaced curved leaf members of aluminum or copper); U.S. Pat. No. 3,326,214 to McCoy (convolutely wound aluminum foil or pleated aluminum foil); U.S. Pat. No. 4,620,537 to Brown (concentric shells of hygroscopic cellulose and felt); U.S. Pat. No. 4,825,863 to Dittmar et al. (electrical heaters and humidifier cartridges); U.S. Pat. No. 2,610,038 to Phillips (spiral wound sheet material forming inspiratory channels with absorbent material attached to or incorporated in the walls of the channel); U.S. Pat. No. 3,333,585 to Barghini et al. (porus hydrophobic fabrics).

Use of hygroscopic materials as inserts for a moisture and heat exchange device for breathing devices are also known; see, e.g., U.S. Pat. No. 4,771,770 to Artemenko et al. (alternating hydrophobic and hydrophilic insert washers); U.S. Pat. No. 3,747,598 issued to Cowans (hygroscopic activated molecular sieve material); U.S. Pat. No. 3,099,987 issued to R. G. Bartlett Jr. (silica gel); U.S. Pat. No. 3,920,009 issued to Olsen (tracheostomatic bandage HME).

Some HMEs rely on condensation and evaporation; see, e.g., U.S. Pat. No. 3,920,009 issued to Olsen.

Earlier medical HMEs consisted of stacked aluminum screens. Later versions of HMEs have employed a fiber mass with a desiccant such as lithium bromide or lithium chloride (an example of such an HME is the ARC™ device made by ARC Medical, Inc. Pharma Systems AB, Sweden). Other HME designs utilize laminar flow structures or quasi-laminar flow structures. In one device, a long strip of corrugated paper, treated with desiccant, is wrapped in a spiral (See, for example, Humid-Vent™ 2 Port, Gibeck-Respiration AB, Uplands Väsby, Sweden). In another device, two long strips of treated paper, each corrugated at about a 45 degree angle with respect to the length of the strip, are placed together. This combined strip is then spiral wrapped. (See, for example, HYGROBAC™ made by DAR, Mirandola, Italy).

HMEs are also known that utilize pleated or folded sheet material (see, U.S. Pat. No. 5,035,236 to Kanegaonkar) along with hygroscopic inserts or bars are also used. (See U.S. Pat. No. 5,320,096 to Hans). Other HMEs for use with medical ventilators include the use of vapor permeable fiber tubes with or without warm water circulated into the housing space around the tubes; see, e.g., U.S. Pat. No. 4,355,636 to Oetjen et al.; UK Pat. No. Application GB 2,082,921 to Benthin; U.S. Pat. No. 4,327,717 to Oetjen et al. Metered tempered sterilized water can also be supplied to the HME; see, e.g., U.S. Pat. No. 5,383,447 to Lang.

There has been considerable effort in developing hygroscopic coatings or treatments for use in HMEs. With current HMEs, the preferred approach is to use water soluble salts such as lithium chloride (LiCl) or calcium chloride ($CaCl_2$) as the hygroscopic material. These materials readily absorb and desorb water vapor, forming a thin water-salt solution on their surface. Since these materials are water soluble, patient moisture may leach the salts, reducing their effectiveness over time. Some liquids such as glycerin, and ethylene glycol readily absorb and desorb moisture and can be used as a hygroscopic material. In order to use these liquids, an HME bed must contain a solid hygroscopic absorbent, such as a paper fiber. As with water soluble salts, the hygroscopic material may leach over time, and the liquids which exhibit a nonzero vapor pressure will evaporate with time. U.S. Pat. No. 5,320,096 further discloses treating strips of heat and moisture exchanging material with LiCl, $CaCl_2$, polyacrylic acid, polyvinyl pyrrolidone, polyvinyl alcohol, or other hydrophilic polymers, glycol or glycerin. However, the hygroscopic treatments are water soluble and can migrate or leach with time.

Partitioning the hygroscopic material with grids of hydrophobic material has been used to prevent flow of the hygroscopic salt; see, U.S. Pat. No. 4,594,860 to Coeliner et al. (a moisture transfer wheel).

Solid crystalline or amorphous inorganic materials are frequently used as desiccants in heat recovery ventilation applications. They have long life and provide excellent moisture return performance. For example, molecular sieves such as silica gel (amorphous silicon dioxide), activated carbon, and zeolites (crystalline sodium aluminosilicate) are often used. The particles are held in place in various ways; see, e.g., U.S. Pat. No. 3,099,987 (screens); U.S. Pat. No. 4,875,520 (bonding technique).

Virtually all presently available HMEs are known to be only partially effective. They do not retain sufficient moisture to prevent drying of the patient's airways. For patient's on long term pulmonary care, the drying of the airways which occurs with presently available HMEs thickens mucous secretions over time to the point where blockage occurs. This is a life threatening situation, often leading to pneumonia. After several days, HMEs must be replaced with active heat and moisturization. There is a great need for a highly effective HME which can provide sufficient moisture retention to the patient to prevent drying of mucous secretions.

It is noted, in addition to the need for HME with high moisture retention, there is a need for a device with low resistance to flow or low pressure drop and low dead volume. By "dead volume" is meant the total internal volume of the HME which is air. At the end of the outbreath, this volume is filled with stale air from the patient's exhalation which the patient breathes back in again on the next in-breath. It is important to keep the dead volume small compared to the total volume of inhaled air so that the patient receives air sufficiently rich in oxygen and low in carbon dioxide. Resistance to flow and large dead volume impede weaning of the patient from the ventilator and subsequent recovery.

Thus, notwithstanding the many known problems with current mechanical systems and the practical design problems of alternative systems, the art has not adequately responded to date with a heat exchanger that utilizes regeneration and allows a high heat transfer between the fluid and the heat exchanger for near room temperature regenerator applications. Further, the art has not produced an HME that can provide sufficient moisture retention to prevent drying of a patient's airways and that has low resistance to flow or low pressure drop and low dead volume. Nor has the prior art produced regenerative heat exchangers utilizing a hygroscopic elastomeric matrix which can directly absorb and desorb a substantial amount of water vapor thereby increasing the heat capacity of the matrix.

SUMMARY OF THE INVENTION

The present invention responds specifically to the long-felt need heretofore unmet by the prior art, and especially with a view to overcoming insufficient moisture retention, high resistance to flow and high dead volume of heat and moisture exchangers for heating and moisturizing respiratory gases during medical artificial ventilation. The foregoing and other advantages of the present invention are realized in one aspect thereof in a heat and moisture exchange device that includes a housing and a regenerative heat and moisture exchanger bed disposed in the housing. The housing has an inlet port for communication to a first fluid source and an outlet port for communication to a second fluid source, and is operatively associated with the bed for directing fluid flow through the bed. The bed includes a matrix of tensioned parallel sheets having substantially parallel flow channels therebetween. The flow channels have an aspect ratio of at least 10 to 1. The flow channels extend substantially parallel adjacent layers of the matrix, and extend substantially parallel to each other. In use, the first fluid source is suitably a ventilation circuit and the second fluid source is a patient's respiratory system.

In another aspect, the present invention discloses a heat and moisture exchange device for use in a medical artificial ventilation system including a housing and an elastomer regenerative heat and moisture exchanger bed disposed in the housing. The housing has an inlet port for communication to a ventilation circuit and an outlet port for communication to a patient's respiratory system, and is operatively associated with the bed for directing fluid flow through the bed. The bed includes a matrix of stretched elastomer and having flow channels therethrough. The matrix includes parallel layers of stretched elastomer sheets. Each layer is generally rectangular and has a layer length dimension. Each sheet has an unstretched sheet length less than said layer length dimension. The bed further includes spacers between the sheets defining substantially parallel fluid flow channels therebetween. Each of the channels has a first rectangular face adjacent a first layer and a second rectangular face adjacent a second opposite layer. The bed includes locking means for locking the sheets and spacers together. The elastomer comprises a material which can be stretched at least 5% and can return to its original shape when stress is removed. In one embodiment of the device, the first rectangular face and the second rectangular face are identically dimensioned.

The invention also provides another embodiment of the device wherein the layers of elastomeric sheets comprise a ribbon of elastomer, having a ribbon width dimension. The ribbon is oriented in a parallel fold pattern creating a plurality of folds with a spacer inserted in each of the folds, and between the folds. The spacers have a spacer length dimension greater than the ribbon width dimension. Each of the spacers has a pair of spacer holes therein, and the spacer holes are spaced at a dimension greater than the ribbon width dimension. The locking means penetrates the spacer holes.

The invention also provides an embodiment wherein the bed comprises a core with the stretched elastomer spirally wound about the core forming elastomer layers, with spacers between the layers forming the flow channels therebetween. The spacers are disposed at uniformly spaced angular position about the core.

In another aspect, the housing further comprises a pair of side plates for maintaining the matrix in a stretched configuration. The locking means of the bed includes end blocks having opposing edges, and the side plates of the housing, also having opposite edges, engages the opposing edges of the end blocks.

The bed of the stretched elastomer may be hygroscopic. Preferably, the bed of the stretched elastomer absorbs at least 36 milligrams of water per liter of exhaled gas and desorbs at least 36 milligrams of water per liter of inhaled respiratory gas.

In yet another aspect of the invention, a heat and moisture exchanger bed includes parallel layers of stretched elastomer sheets, spacers and locking means for locking the sheets and spacers together. Each layer is generally rectangular and has a layer length dimension, and each sheet has an unstretched sheet length less than the layer length dimension.

The spacers between the sheets define substantially parallel fluid flow channels therebetween. Each channel has a first rectangular face adjacent a first layer and a second rectangular face adjacent a second opposite layer. The elastomer sheets of the bed include a water vapor transmitting elastomeric matrix charged with a hygroscopic material. In use, an air stream containing water vapor is directed through the flow channels and over the sheets to effect a change in temperature and moisture content in the air stream.

In another aspect of the invention, the elastomer sheets of the bed are hygroscopic, and absorb and desorb the water vapor from the air stream.

In yet another embodiment of the invention, the bed has a predetermined heat capacity and the elastomer sheets absorb an amount of water vapor sufficient to increase by at least 25% the heat capacity of the bed.

In a further embodiment of the present invention, each of the elastomer sheets comprises a base elastomer material and a hygroscopic elastomer material coated upon the base material. The hygroscopic elastomer material is capable of absorbing and desorbing the water vapor.

In yet another embodiment of the present invention, each of the elastomer sheets includes a base elastomer material and a hygroscopic, moisture-transmitting elastomer material charged with a hygroscopic material and coated on the base material. The elastomer material charged with the hygroscopic material absorbs an amount of said water vapor sufficient to increase by at least 25% the heat capacity of the bed.

The present invention also provides a method of manufacturing a spiral elastomer regenerative heat and moisture exchanger bed. The method includes: (a) winding spirally an elastomer strip material about a core to form a plurality of spirally wound elastomer layers where the core has discrete segments; (b) positioning and securing spacers between the layers at uniformly spaced angular positions about the core; (c) expanding the segments of the core and stretching the layers; and (d) locking the segments of the core in an expanded state and maintaining the layers in a stretched position.

The present invention further provides an elastomer regenerative heat exchange device comprising at least one elastomer member. The elastomer member comprises water vapor transmitting elastomeric matrix charged with a hygroscopic material. The elastomer member is capable of absorbing and desorbing moisture. The device can further comprise a nonelastomeric member, wherein the elastomer member is coated on the nonelastomeric member. The bed matrix may be uniformly charged with the hygroscopic material.

In still yet a further aspect of the invention is an elastomer regenerative heat exchange device comprising at least one elastomer member. The elastomer member comprises a base elastomer material and a hygroscopic, water vapor-transmitting material coated on tile base elastomer material. The hygroscopic, water vapor-transmitting material comprises a hygroscopic, water vapor-transmitting elastomeric matrix charged with a hygroscopic material. The device has a predetermined heat capacity and the hygroscopic, water vapor transmitting material absorbs an amount of water vapor sufficient to increase by 25% or more the heat capacity of the device.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which:

FIG. 6 is a top view of the device of FIG. 4; the bottom view is identical;

FIG. 7 is a right side view of the device of FIG. 4;

FIG. 8 is a front view of the device of FIG. 4 with the housing partially cut away to show the orientation of a portion of the elastomeric bed HME;

FIG. 12' is an L-shaped spacer for use in the elastomer bed HME of FIG. 12;

TABLE 1

Figure 2:
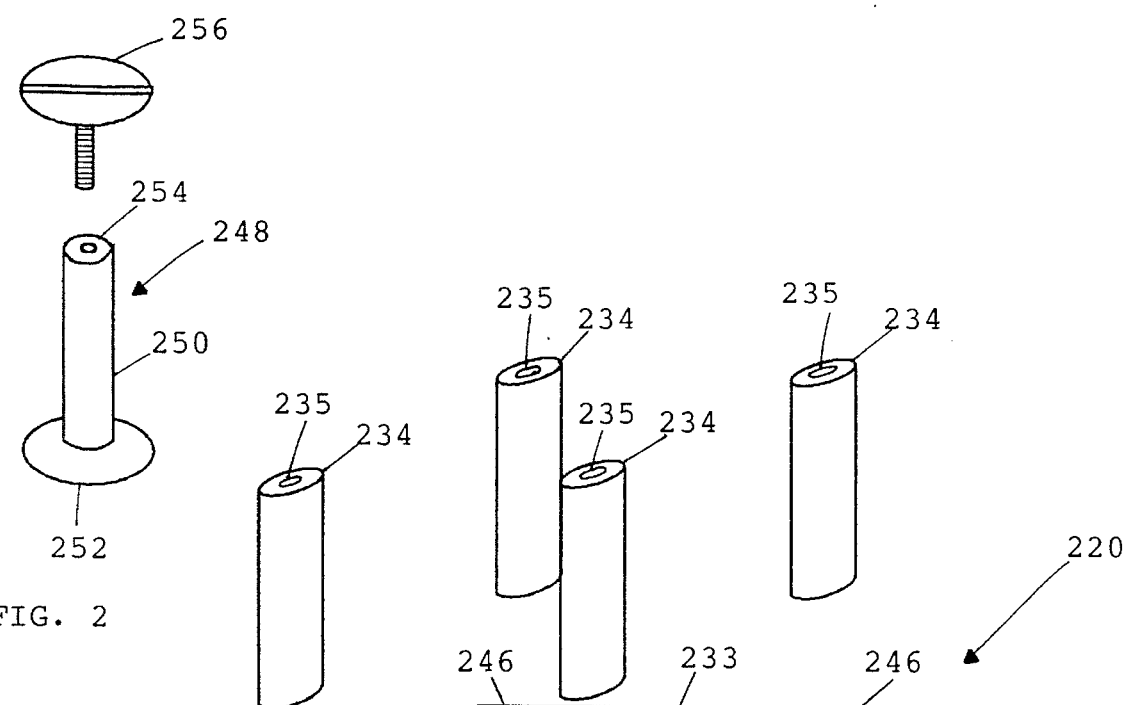
FIG. 2 is an alternative rod structure.

Required Ntu for Given HME Moisture Return

| Moisture Return in mg water/l air | Moisture Return Effectiveness | Ntu Required (Le = 1) |
|---|---|---|
| 36 | 81.63% | 8.89 |
| 38 | 86.17% | 12.46 |
| 40 | 90.70% | 19.51 |

A moisture return of about 39 milligrams of moisture (water vapor) per liter of air (mg/L) will be sufficient to eliminate the need for active heat and moisturizers for most patients. To obtain this level of moisture return, about 15 Ntu (assuming a Lewis Number of 1) are required. On the other hand, taking a "worst-case" value of four for the Lewis Number, 60 Ntu would be required for this moisture return. This is the value of Ntu assumed in the present design.

The heat capacity requirement, for the bed, comes from numerical simulations of regenerators (see Schmidt and Willmot, Thermal Energy Storage and Regeneration, McGraw-Hill, 1981). If the bed has too little heat capacity, as described hereinbefore, thermal "break through" will occur, i.e., the bed loses its temperature gradient prior to the end of flow in either direction. The bed temperature becomes uniform and equivalent to the temperature of the air entering the bed, causing the temperature of the air leaving the bed to be the same as the temperature of the air entering the bed. Needless to say, too little heat capacity compromises the effectiveness of the HME.

Further, the total heat capacity of the bed should be accessible. Because the thermal conductivity of materials used for the sheets or layers of the bed is typically low, if the sheets are too thick, the center of the sheet will be thermally isolated from the surface and, therefore, the air stream. Thus, the sheets must be sufficiently thin to permit the heat to diffuse into and out of the sheet sufficiently rapidly with respect to the time period of fluid flow reversal, i.e., in the medical application, the time period of a respiration inhalation/exhalation cycle.

The thermal diffusivity of a material can be used to determine how thin a sheet must be so that the center is not thermally isolated from the surface. Thermal diffusivity is the thermal conductivity of the material divided by the heat capacity per unit volume. For example, the thermal diffusivity of natural rubber is about 0.001 cm$^2$/sec (centimeter squared per second). A thermal diffusion time of 0.1 second occurs when the half-sheet thickness is less than 0.01 cm (0.0039 inch). Any sheets thinner than 0.020 cm (0.008 inch) will not have any inaccessible heat capacity.

Required Heat Capacity and Mass of an Adult HME Bed

The total heat contained in a patient's breath is the sum of the sensible heat (temperature of the breath) and latent heat (heat required to evaporate the amount of water given by the moisture content of the breath). This sum is given more directly by the enthalpy of the breath, measured in Joules per gram (J/g) of dry air. For estimating the required heat capacity for an HME suitable for an adult, a body temperature of 37° C. (98.6° F.) and a room temperature of 20° C. (68° F.) was assumed. It was also assumed that the patient's breath is fully humidified (100% Relative Humidity (RH)), and ventilating air is perfectly dry to (0% RH). The required average specific heat capacity of the bed (in Joules per gram-degree Celsius; J/g°C.) is the enthalpy span (in J/g) divided by the temperature span (in degrees Celsius). The temperature span is the arithmetic difference between the two temperatures. The enthalpy span is the arithmetic difference in enthalpy at the two different temperatures. Table 2 shows the standard enthalpy values and shows that the average specific heat capacity of the fluid is 7.2 J/g °C.

TABLE 2

Data for Heat Capacity Calculation

| | |
|---|---|
| Enthalpy at 37° C., 100% RH | 143 J/g |
| Enthalpy at 20° C., 0% RH | 20.1 J/g |
| Enthalpy span | 122.9 J/g |
| Temperature span | 17° C. |
| Average heat capacity of the fluid | 7.2 J/g°C. |
| Approximate ratio of fluid to bed heat capacity | 0.35 |

The mass of heat exchanger material, e.g., elastomer, required is a function of the ventilation tidal volume and the heat capacity of the material used. If an adult tidal volume is 1 liter at 0% humidity and 20° C., the mass of the ventilating air is 1.2 grams. Thus, the total fluid heat capacity at one liter tidal volume is 7.2 J/g°C. times 1.2 g or 8.6 J/°C. Therefore, the total bed heat capacity is 8.6 J/°C. divided by 0.35, or 24.7 J/°C.

While elastomers are preferred for the tensioned sheets of the bed of the present invention, the heat capacities of elastomers are seldom known by manufacturers. Natural rubber has been reported in the literature to have a specific heat capacity of about 2.0 J/g°C. Water has a specific heat capacity of about 4.22 J/g°C. It was assumed herein that other elastomers have heat capacities close to that of natural rubber. The required mass of elastomer in an elastomer matrix bed is then 24.7 J/°C. divided by 2.0 J/g°C. or 12.4 grams of elastomer. Further, if the elastomer used is moisture absorbing and absorbs 100% of its weight in water, the average specific heat capacity of the material is about 3.1 J/g°C., leading to a required bed mass of 7.9 grams, of which only 4.0 grams is elastomer. Table 3 summarizes these parameters.

TABLE 3

Bed Mass at 1 Liter Tidal Volume for Two Different Elastomers

| | |
|---|---|
| Required total heat capacity at 1 liter tidal volume | 24.7 J/°C. |
| Bed mass for elastomer (2.0 J/g°C. heat capacity) | 12.4 g |
| Bed mass for 100% water absorbing elastomer | 7.9 g |

A significant change in heat capacity is exhibited by an elastomer which absorbs water and thereby increases the heat capacity of the elastomer by 25% or more.

The relationships for pressure drop per unit length and heat transfer coefficient (from which Ntu is calculated) are well known for laminar flow through channels with two infinite parallel walls. From these, relationships were developed for pore volume and pressure drop for given values of Ntu, air flow rate, tidal volume, and the bed's physical parameters of length and bed spacing. Table 4 shows reasonable design parameters for an adult and a neonatal elastomer bed HME:

DETAILED DESCRIPTION

This invention relates generally to heat transfer devices, i.e., heat exchangers, enthalpy exchangers, heat and moisture exchangers, and more specifically, to medical heat and moisture exchangers utilizing the regenerator principle. More particularly, the present invention is a high performance, low cost, regenerator/heat exchanger matrix or bed well-suited for medical application. Accordingly, the present invention will now be described in detail with respect to such endeavors: however, those skilled in the art will appreciate that such a description of the invention is meant to be exemplary only and should not be viewed as limitative on the full scope thereof.

The regenerator/heat exchanger bed in accordance with the present invention includes numerous tensioned parallel spaced apart material layers or plates, which define fluid flow channels therebetween, i.e., adjacent spaced apart parallel plates define a flow channel therebetween. The resulting bed is a parallel plate matrix with high porosity, and narrow, uniform, unobstructed flow channels. As used herein, the terms "porosity" or "porous" are meant to refer the fact that flow channels are present in the bed matrix. The term "tensioned" is meant to refer to the material plates as being taut. As such, the plates do not substantially flex or deform in response to fluid flow or pressure drop.

The parallel plate configuration of the bed is the best possible for a laminar flow regime. Fluid flow is through the flow channels and over the layers or sheets, and proceeds in a reciprocating fashion. The plate spacing is made very fine with a high degree of uniformity from one flow channel to the next. In addition, the layers or sheets have high heat capacity. The bed is ideal for near room temperature regenerator applications.

The performance of a regenerator or heat exchanger is measured in terms of heat transfer per unit pressure drop, and the geometry of the flow channels through which the fluid flows significantly affects performance. The dimensionless number, $$\alpha = \frac{St \, Pr^{2/3}}{f}$$

where St is the Stanton number, Pr is the Prandtl number and f is the friction factor, is used as a measure of the heat transfer per unit pressure drop. Kays and London (W. M. Kays and A. L. London, *Compact Heat Exchangers*, McGraw-Hill, New York 1984) list the following $\alpha$ values for different fluid flow channel geometries:

| Channel Geometry | $\alpha$ |
|---|---|
| Infinite parallel | 0.386 |
| Rectangular 4 to 1 aspect ratio | 0.328 |
| Circular | 0.307 |
| Square | 0.286 |
| Triangular | 0.263 |

It is seen that channels which are formed by two infinite parallel planes have the highest heat transfer per unit pressure drop. The bed in accordance with the present invention has an aspect ratio of at least 10 to 1, and preferably more than 100 to 1. As such, the present bed closely approximates the optimal infinite parallel plane geometry.

Plates for the bed matrix are suitably constructed of any material that can be tensioned. Preferred are elastomers, typically materials which can experience a 5% stretch and return to the undeformed configuration, e.g., natural and synthetic rubbers. The preferred materials in accordance with the present invention have a tensile strength greater than about 650 psi, a tear resistance greater than about 70 pounds per inch, and a specific heat capacity of about 2 Joules per gram per °C. (J/g° C.).

FIGS. 1–22 depict preferred embodiments of a bed matrix in accordance with the present invention, used as an enthalpy exchanger for retaining heat and moisture from respiratory gases for use in medical artificial ventilation. The heat and moisture exchanger works on the same principle as a regenerative air-to-air heat exchanger.

Operation of a Medical HME

In medical use, warm moist breath, deficient in oxygen and high in $CO_2$, is forced through the matrix of an HME in one direction. After an amount of air has flowed equivalent to the "tidal volume," cool, dry air, high in oxygen and low in $CO_2$, flows in the opposite direction. "Tidal volume" means herein, and in the art, the total volume of air that is inhaled in a single breath. Except in unusual cases, the flow is well balanced, i.e., the volume of air flowing into the patient's lungs is equal to the volume of air flowing out of the patient's lungs. After repeated breaths, a temperature gradient develops across the matrix. The warm moist breath cools as it progresses through the matrix and moisture condenses on the matrix. (If the matrix contains a desiccant, the moisture will condense even when the vapor pressure is below saturation, or the relative humidity is below 100%.) As the breath cools and moisture condenses, heat and mass (water) are delivered to the matrix. On the return flow, during inhalation, cool dry air from the ventilator is warmed by the matrix and the moisture absorbed by the matrix during exhalation, is released. The bed matrix is repeatedly cooling after being warmed and drying after being wetted, hence the term "regenerator."

In a regenerative heat exchanger, it is important for the matrix to have high heat capacity otherwise the matrix will lose its temperature gradient before flow has reversed. Exhaled air will no longer be cooled, defeating the heat exchange effectiveness. During inhalation, dry cool air will not be warmed toward the end of the breath. Even if the cool air has high relative humidity, the absolute humidity will be low and moisture return efficiency will suffer. For example, if the inhaled air toward the latter part of the breath enters the patient at 20° C. (68° F.) and 100% relative humidity, it has a moisture content of 16.3 mg of water per L of air. This moisture content is low compared to the 44 mg of water per L of air for saturated air at 37° C.

For a highly effective HME, the total heat capacity of the regenerator bed must be greater than about three times the total heat capacity of the fluid flowing over the regenerator plates between flow reversals. If this inequality holds, then the thermal effectiveness can be calculated with a high degree of accuracy from the following equation:

Thermal Effectiveness=$Ntu/(Ntu+2)$ where Ntu is the number of heat transfer units. The moisture transfer effectiveness is given by:

Moisture Transfer Effectiveness=$(Ntu/Le)/((Ntu/Le)+2)$, where Le is the Lewis Number which can range from one in the ideal case to as high as about four. For high HME moisture return value, an bed must have high Ntu. Table 1 shows this relationship for several values of moisture return.

TABLE 4

Design Parameters for Adult and
Neonatal Elastomer Bed HMEs

|  | Adult | Neonatal |
| --- | --- | --- |
| Heat transfer units ($N_{Tu}$) | 60 | 300 |
| Flow (liters/min.) | 60 | 5 |
| Tidal volume (liters) | 1 | 0.03 |
| Bed length (cm) | 2.9 | 0.5 |
| Sheet spacing, stretched (cm) | 0.031 | 0.008 |
| Sheet thickness, stretched (cm) | 0.012 | 0.005 |
| Pore volume (cc) | 32.0 | 0.8 |
| Pressure drop (cm of water) | 0.6 | 1.0 |
| Cross-sectional area (cm$^2$) | 15.2 | 2.6 |
| Total elastomer mass (g) | 13.3 | 0.55 |

In the bed design in accordance with the present invention, the channels have length, in the flow direction, which is the same as the bed length. The channel width is the same as the sheet spacing. The channel height can vary, depending on how the cross-sectional area is dimensioned. A shorter channel height means that more channels are needed.

The mass of elastomer in the adult HME is slightly larger than the required minimum of 12.4 g previously computed using the estimated heat capacities.

The pore volume is the cross-sectional area times the bed length minus the volume of the elastomer. The pore volume is approximately the volume contained in the flow channels. The total dead volume will be greater since it includes the internal volume of the end cap of the housing placed around the elastomer matrix bed. The design of the housing for the bed can, however, minimize this additional volume.

Since the required minimum is linearly proportional to the tidal volume, the minimum elastomer mass for the neonatal HME can be calculated and is 0.37 g. The neonatal design has very fine structure. The tensioned sheet thickness is about 2 mils, and the sheet spacing is about 3 mils.

PREFERRED EMBODIMENTS

Reference is now made to FIGS. 1–8 depicting a complete assembly generally designated by reference numeral 200 which includes a regenerator/heat and moisture exchanger bed in accordance with the present invention and generally designated as 220 and a housing 260. This bed HME is referred to as a "stack and stretch" design. The bed 220 in accordance with the present invention includes a porous matrix 222 having parallel plates 224 with fluid flow channels 225 in between the plates 224. Each of the flow channels 225 has a constant dimension throughout. The plates 224 are separated by spacers 228 of equal thickness that lay along opposite edges 230 of the plates 224. The plates 224 are layers of tensioned sheets 226, e.g., stretched elastomer sheets. As used herein, the term "spacer" is meant to refer to any thing or device that can separate the plates. For example, a spacer 228 may be a separate shim or sheet or may be a portion of the elastomer sheet that is thicker than the plate proper. The spacers 228 may also be made of any nonelastomeric material such as paper, treated paper, plastics, metal, etc. It is desirable that the spacers 228 are flexible and not brittle.

Figure 1:
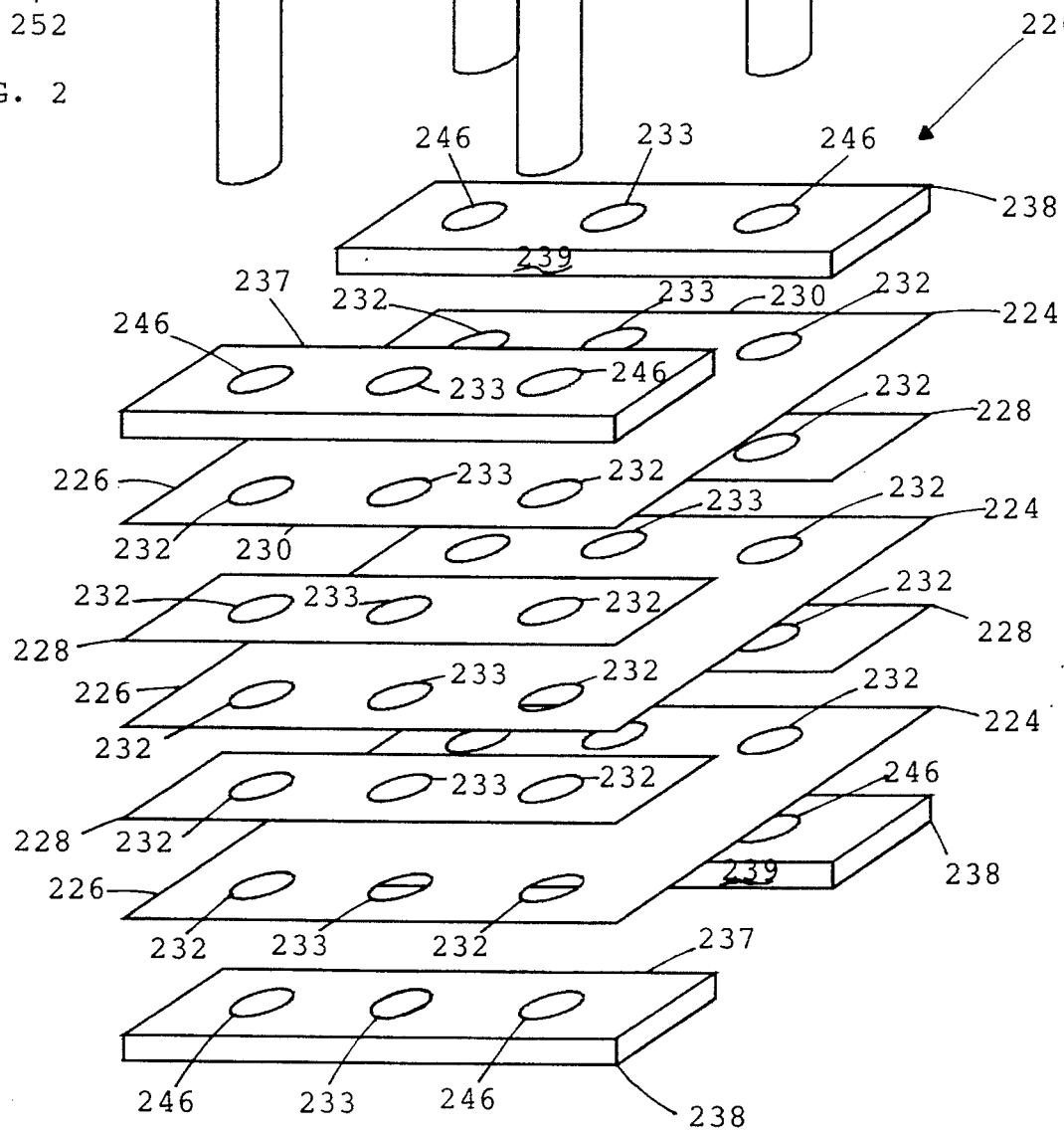
FIG. 1 is an exploded view of the elastomer sheets, the spacers, the end blocks and the rods of the elastomer bed stack and stretch heat and moisture exchanger for medical ventilation.

FIG. 1 shows an exploded view of the spacers 228 and the elastomer sheets 226. The spacers 228 are suitably adhered to the elastomer sheets 226. The elastomer sheets 226 and spacers 228 are shown with holes 232 for the insertion of threaded rods 234. An additional set of holes 233 in the sheets 226, spacers 228 and rectangular blocks 238 may be used for purposes of stretching assembly of the device 220.

The tensioned sheets 226 are separated by two nonelastomer spacers 228 along opposite edges, as illustrated in FIG. 1. The method of assembly used is as follows: four rods 234 are inserted into the appropriate openings 246 in two of the rectangular end blocks 238 shown in FIGS. 3 and 5. Each rectangular end block 238 has a side face 239 which faces opposite and parallel to the same side face 237 of the corresponding rectangular end block 238. The two rectangular end blocks 238 are then held flat such that the four rods 234 protrude vertically, and are spaced such that a sheet 226 can be easily placed over the rods 234, without being tensioned, with each of the four holes 232 in the sheet 226 sliding over the corresponding rod 234.

Matrix 222 is then assembled by alternately placing sheets 226 and spacers 228 over the rods 234 until the desired thickness of the matrix 222 is achieved. The two remaining rectangular blocks 238 are then put in place. The rods 234 are then made to adhere to the end blocks 238, for example, by swaging. Rivets are also suitably used. Preferably, as is shown in FIG. 2, hardware such as screw posts 248 are used in place of the rods 234. Screw posts 248 are rods 250 which have one flattened nail head-like end 252 and a second drilled tapped end 254. A flat head screw 256 is threaded through the drilled tapped end 254 of the screw post 248. By threading each screw 256 in each tapped end 254 in each screw post 248 and tightening the screws 256, after the remaining two rectangular blocks 238 are put in place, the matrix stack 222 is secured for tensioning.

In some cases, it has been found to be easier to first glue a spacer to a sheet, then punch the holes 232, 233. Suitable adhesives for the spacers include Superglue™ especially if the spacers are plastic. A masking tape, e.g., Tuck Tape™, New Rochelle, N.Y., was also found to work well. The masking tape was applied to both sides of the sheet, instead of just one side. Adhesive bonding may be used to fix two spacers 228 to each elastomer sheet 226, or alternatively the entire stack 222 may be assembled and the clamping force, alone, applied by the rectangular blocks 238 and rods 234, holding the elastomer sheets 226 to the spacers 228. Both methods have been used successfully.

As explained hereinbefore, materials suitable for construction of the parallel plates or sheets of the matrix are materials that can be made taut and resist tear, typically a material that can be tensioned or stretched to 1%–2% of its original shape. Such materials suitably include, for example, elastomers, and some plastic sheeting such as vinyl and polyethylene. Preferred are elastomers, which, as used herein, are materials which can be stretched at least about 5% and return to their original shape when the stress is removed. Elastomers suitably include, for example, latex, polyurethane, neoprene, silicone rubber, hycar, or thermoplastic rubbers. In searching for inexpensive elastomers, a number of medically approved urethanes, in sheet form, are commercially available. Silicon rubber is also available in medically approved sheet form, however, it is typically several times the price of the urethanes. Some urethane sheeting (and silicon rubber sheeting) have high slope of the stress vs. strain (force vs. elongation) curve. Elongations of as little as 5 to 10% can produce flat taut sheets in these cases. Further, many elastomers are typically loaded. By "loading" is meant that material typically in particle form is added to the elastomer prior to curing or vulcanization. Loading is done for various purposes. Often, it is done to reduce cost by replacing the more expensive elastomer with a cheap filler. Loaded elastomers usually have less stretch than pure elastomers. Loaded elastomers are also comprehended in the scope of the invention.

Materials suitable for construction of the bed in accordance with the present invention can also be defined in terms of physical properties, i.e., a tensile strength greater than 650 pounds per square inch, a tear resistance greater than 70 pounds per inch, and an elastomeric elongation of 5% or greater.

Figure 3:
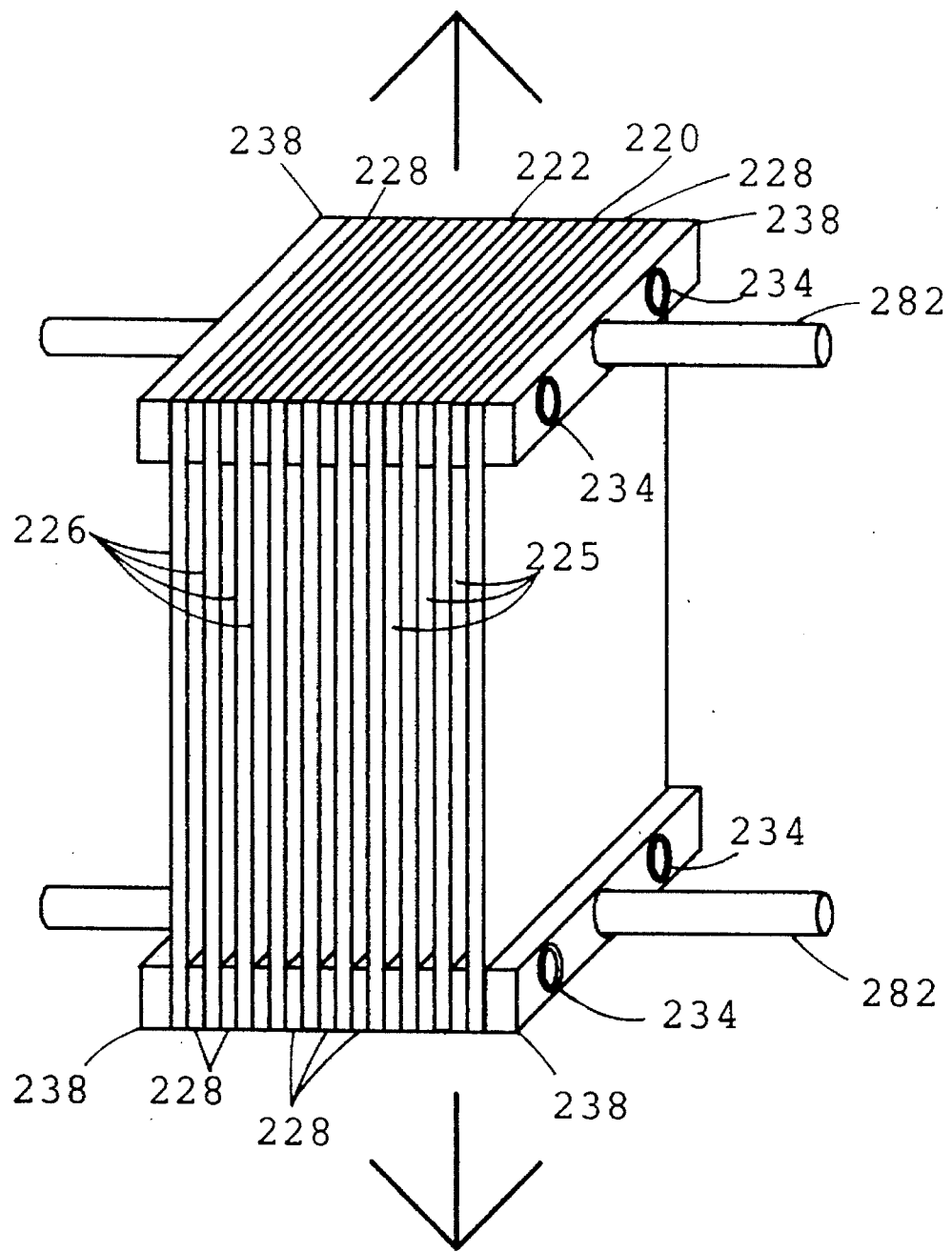
FIG. 3 is the elastomer bed HME of FIG. 1 illustrating a method of stretching the elastomer bed for the final assembly using temporary rods.

As is shown in FIG. 3, after the bed 220 is made with the sheets 226 in a relaxed state, the matrix 222 is tensioned and hardware is placed to hold the sheet taut. Temporary rods 282 are inserted through the openings 233 for this purpose. The arrows show the direction of the tension, i.e, stretch. The tensioned sheets 226 become taut flat plates, separated at precise and equal distances, to form a tensioned bed matrix 259.

The additional openings 233 help reduce the weight of the bed 220. The tensioned plate bed 259 is placed in the housing 260 which holds the tension.

If rods 234 used are hollow, the openings 235 in the rods 234 can be used to stretch and hold tensioned bed matrix 259 at the time the housing 260 is placed.

Figure 4:
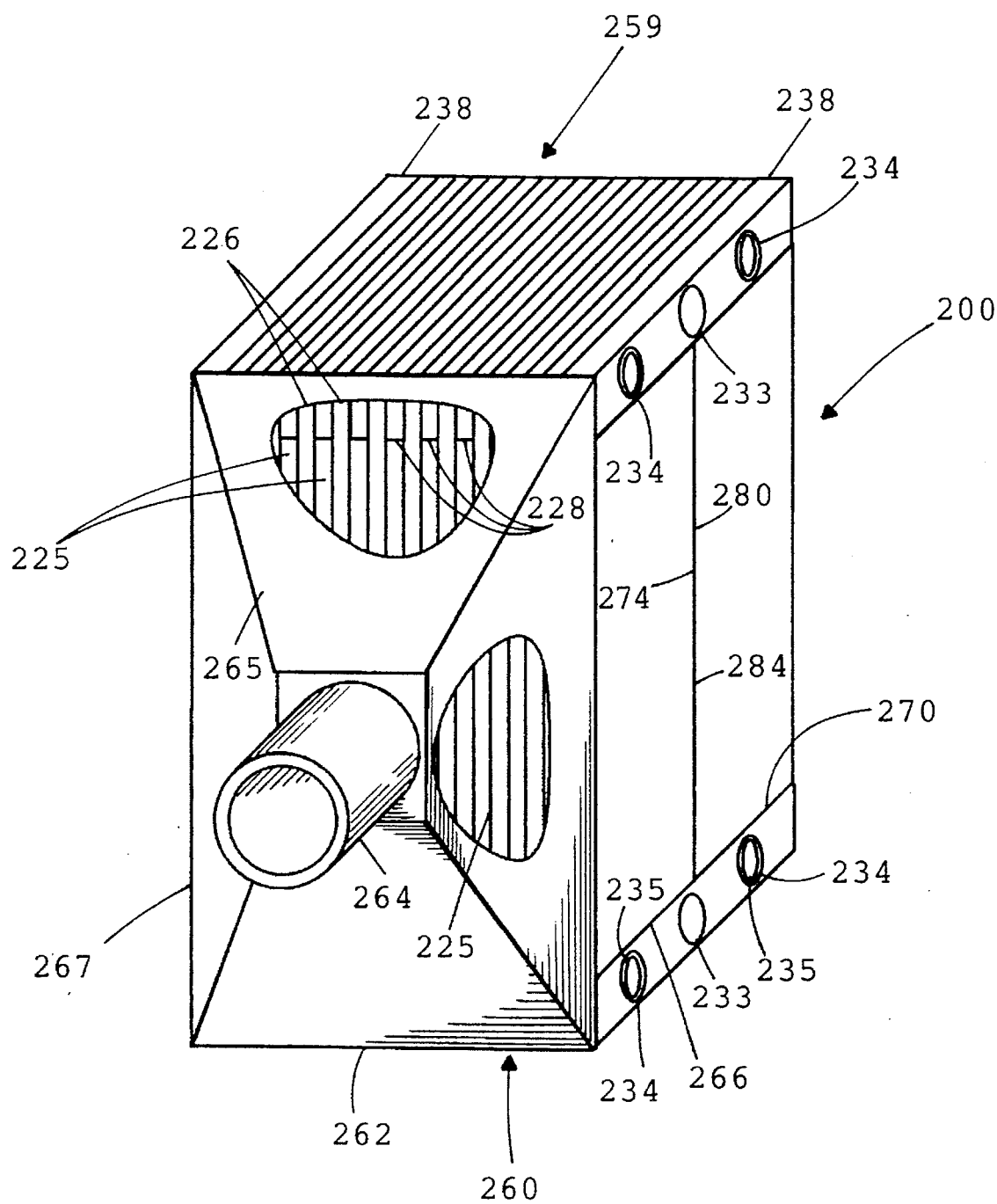
FIG. 4 is a perspective view of the heat and moisture exchanger device for medical ventilation showing the elastomer bed of FIG. 1 in a housing; the housing is cut-away to show the detail of the spacers, the flow channels, and the elastomer sheets of the HME.
Figure 5:
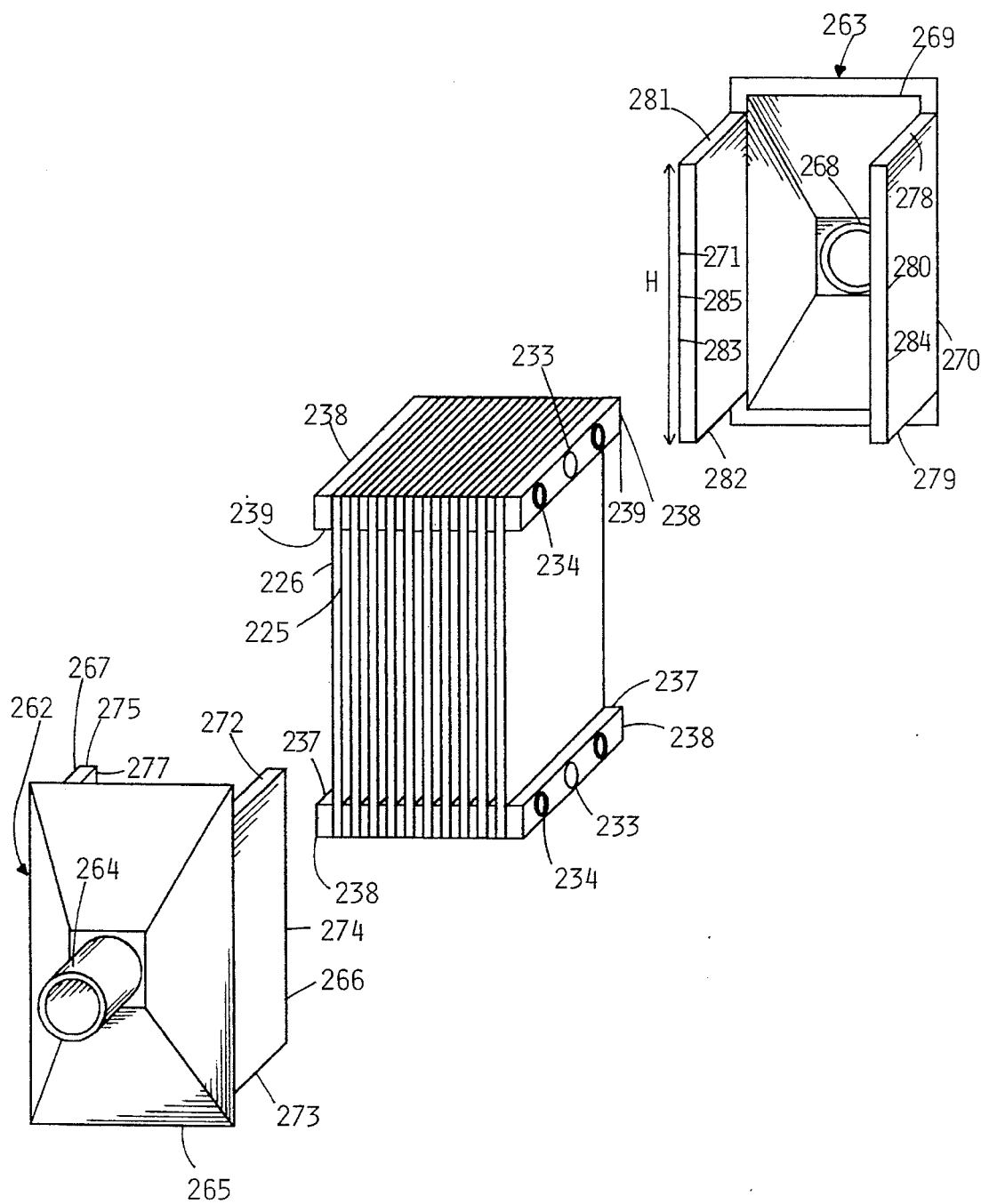
FIG. 5 is an exploded view of the device of FIG. 4.

An example of a complete assembly 200 suitable for transferring heat and moisture in exhaled respiratory gas to inhaled respiratory gas is shown in FIG. 4 in perspective view and in FIG. 5 in exploded view. FIGS. 6, 7, and 8 show the assembly 200 in top, side and front view. The complete heat and moisture exchange device 200 includes housing 260 and elastomer regenerative bed 259 mounted in housing 260. The flow housing 260 has two flow end caps 262 and 263. Each flow end cap 262, 263 has a tubular opening and a plenum. Each flow end cap 262, 263 has a pair of identically dimensioned side plates which provide the structural support to hold the bed matrix 259 in the tensioned or taut position. These side plates also provide flow control, forcing air to flow through the flow channels between the parallel sheets.

Housing flow end cap 262 has a tubular opening 264 penetrating and protruding from a plenum 265. Two identically dimensioned parallel side plates 266, 267 having a height "H" extend outwardly from plenum 265 and in a direction opposite that of the protruding tubular opening 264. Flow end cap 263 has a tubular opening 268 penetrating and protruding from a plenum 269. Two identically dimensioned parallel side plates 270, 271 having a height "H" extend outwardly from the plenum 269 and in a direction opposite that of the protruding tubular opening 268.

Each side plate 266, 267, 270 and 271, respectively, has edge faces extending outwardly from the plenum. These include an upper edge face, a parallel lower edge face and an edge face perpendicular to both the upper edge face and the lower edge face. Thus, side plate 266 has an upper edge face 272, a lower edge face 273, and a perpendicular edge face 274. Side plate 267 has an upper edge face 275, a lower edge face 276, and a perpendicular edge face 277. Side plate 270 has an upper edge face 278, a lower edge face 279, and a perpendicular edge face 280. Side plate 271 has an upper edge face 281, a lower edge face 282, and a perpendicular edge face 283.

To maintain the bed matrix 259 in the tensioned position, the upper edge faces 267, 272, 278 and 281 slide under rectangular end block faces 239 and the lower edge faces 273, 276, 279 and 282 slide over rectangular end block faces 237. The height "H" of side plates 266, 267, 270 and 271 is sufficient to maintain the required tension in the sheets 226. The side plates 266, 267, 270 and 271 also provide flow control, forcing air to flow through flow channels 225 between sheets 226.

As pairs of side plates 266, 267, 270, and 271 are engaged against the faces 237, 239 of the rectangular end blocks 238, the perpendicular edge faces of the side plates move to an abutting position forming separation lines 284, 285. Perpendicular edge faces 280 and 274 abut to form separation line 284; perpendicular edge faces 277 and 283 abut to form separation line 285. FIG. 7 shows a side view of the assembled HME in its housing with the positioning rod 282 removed. Housing 260 separation line 284 indicates where edges 274, 280 of sidewalls 266, 270 abut.

For an adult HME, the end blocks of the bed 259 and the flow end caps 262, 263 including side plates 266, 267, 270 and 271 are suitably made of acrylic and Lexan™ plastic. These plastics are strong and yet lightweight while being poor conductors of heat, a desirable characteristic for this application.

In operation, one of the tubular openings 264, 268 mates with the end of the endotracheal tube (not shown), acting as an outlet port. The other tubular opening 268, 264 mates with a Y-connector (not shown) of the ventilating machine (not shown), acting as an outlet port.

FIGS. 9–12 illustrate another embodiment of the present invention the spiral wound bed, referred to herein as "a spiral wrap." As was previously described in applicant's issued U.S. Pat. No. 5,339,653, a ribbon, e.g., an elastomer ribbon, is fed, under tension, onto a core shaped like a polygon. The start of the ribbon is adhered to the core with adhesive or some other method. Spacers are placed at the corners of the polygon, prior to the next layer of elastomer passing that corner. After the wrap is finished, the end of the ribbon is adhered to the elastomer layer just below it.

In U.S. Pat. No. 5,339.653, the spiral-wrap core is considered for use as a rotating wheel regenerator, typically used for continuous energy recover ventilation in a commercial or residential building. In the elastomer bed HME for use in medical artificial ventilation, since the flow is naturally reciprocating, the entire core is static, in a tightly fitting housing, and acts as a single regenerator element. The separate elastomer regions, the number of which correspond to the number of sides of the polygon, act in parallel.

Figure 9:
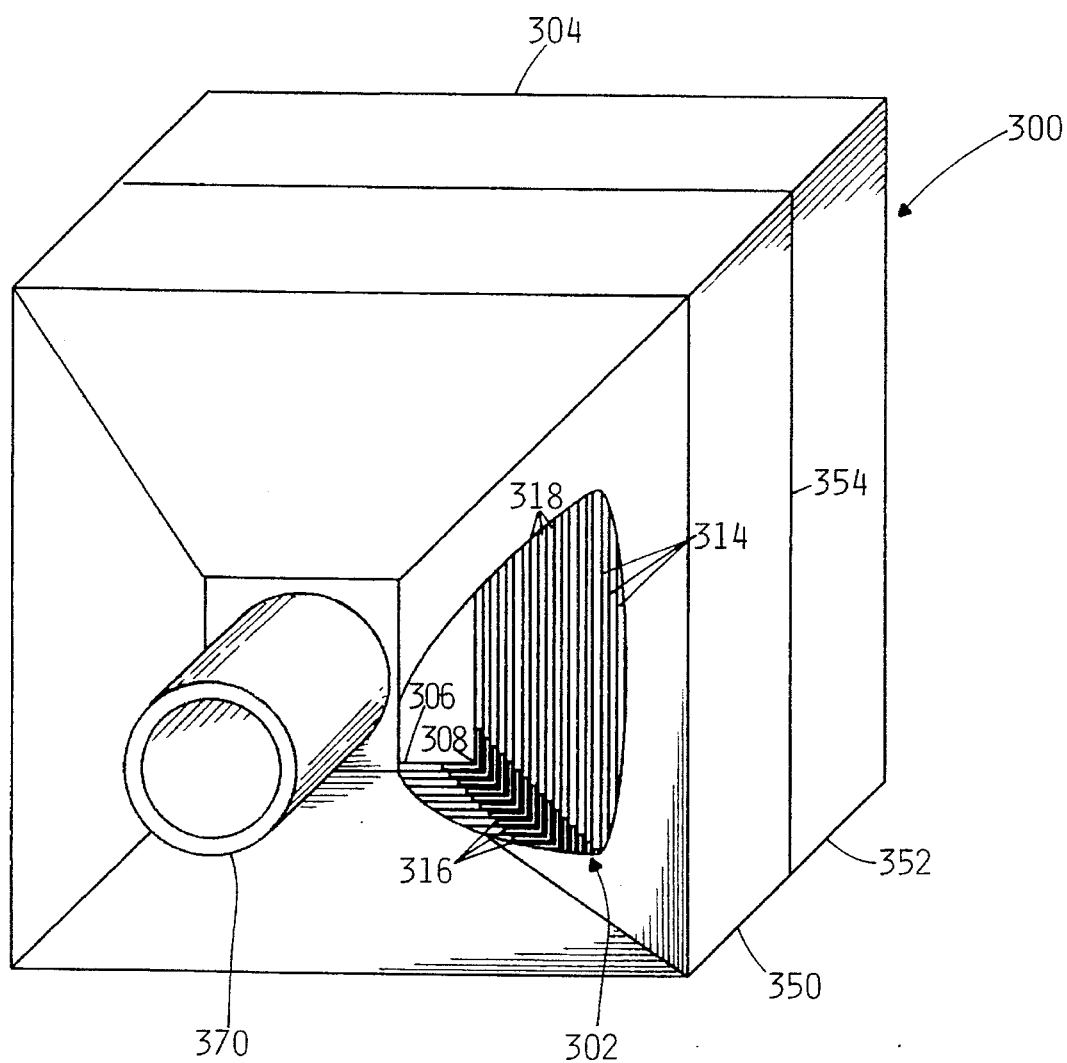
FIG. 9 is a perspective view of another embodiment of the device of the present invention showing an elastomer bed heat and moisture exchanger for medical ventilation in a housing; the cut away lines in the housing show the detail of the spacers, the flow channels and the elastomer sheets of the elastomer bed HME.

FIGS. 9–12 of the present application illustrate a heat and moisture exchange device 300 having a square spiral wound regenerator heat and moisture exchanger 302 for transferring heat and moisture from exhaled respiratory gas to inhaled respiratory gas. FIG. 9 is a perspective view of the present invention showing a bed 302 for medical ventilation in a square housing 304; the cut away lines in housing 304 show spacers 316, flow channels 318 and sheets 314 of the square spiral-wrap bed 302.

The square spiral wrap bed 302 may be made by the method just discussed where a core 306 is rotated about a shaft (not shown) while wheels (not shown) maintain a constant tension in a ribbon 312 as it feeds. Ribbon 312 in tension is shown by reference numeral 314. Spacers 316 are added at a specific location along ribbon 314. The spacers 316 are thus disposed at uniformly spaced angular positions 308 of the core 302. The polygon core 306 is square, having four angled corners 308. Preferably, the spacers 316 are right angled or "L" shaped with the spacers placed in correspondence with the corners 308 of the square core 306 If glue is added to both sides of the spacer 316 prior to contact with ribbon 312, the square spiral wound bed 302 will not unravel when the ribbon 312 is cut.

Figure 10:
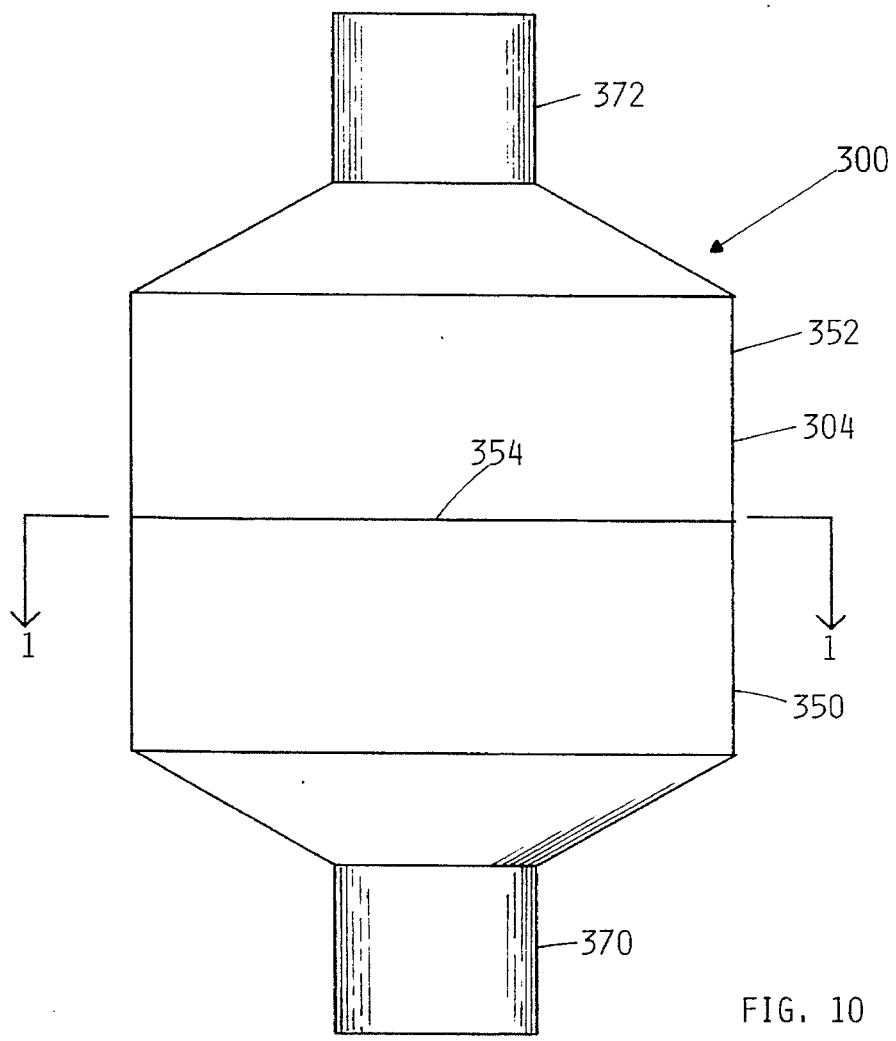
FIG. 10 is a top plan view of the housing of the device of FIG. 9 with the section line 1—1 drawn through the housing separation line; the bottom view is identical.
Figure 12:
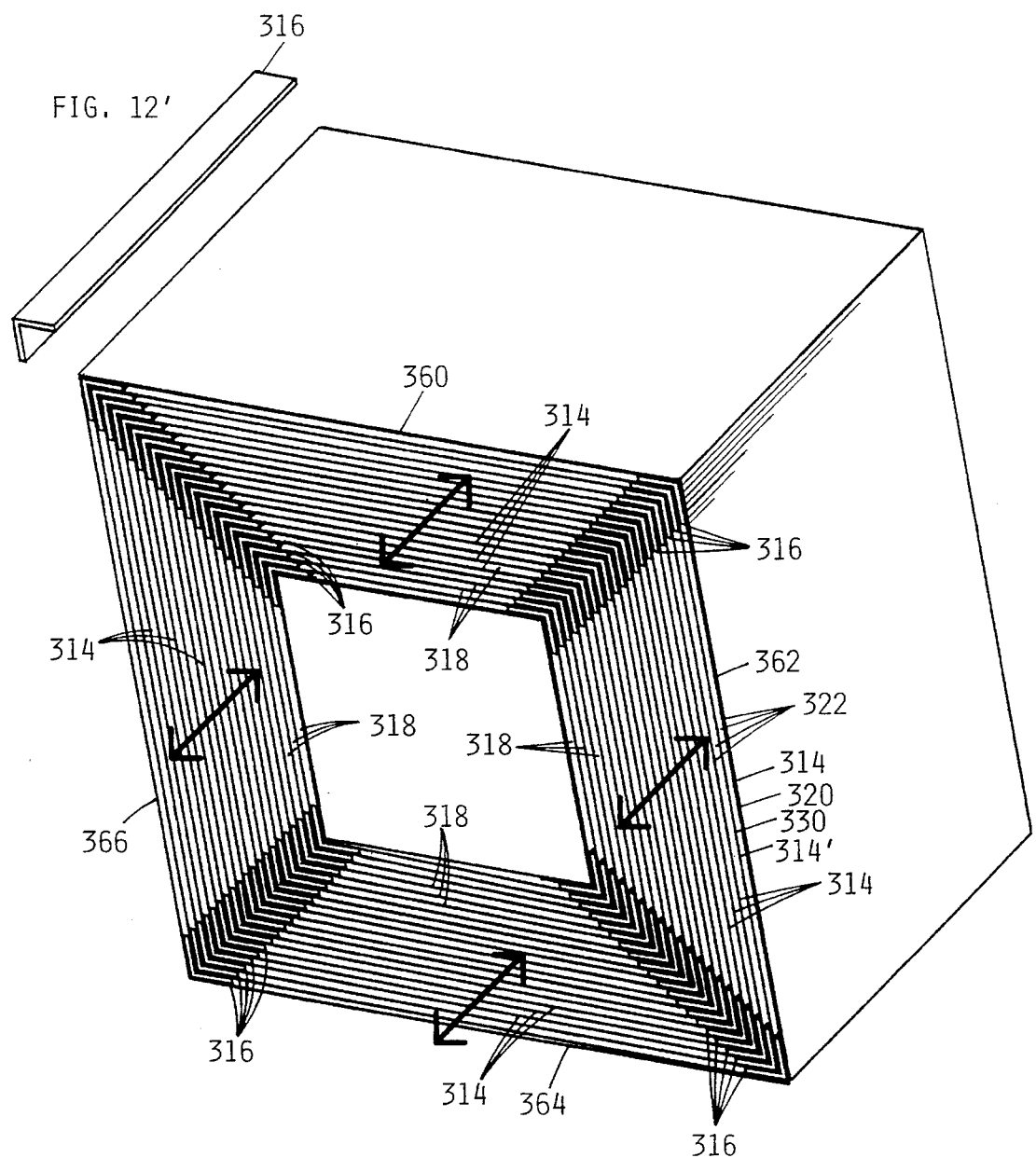
FIG. 12 is a perspective view of the square spiral wrap HME elastomer bed of FIG. 9 showing the direction of air flow through the flow channels of the elastomer bed HME.

FIG. 12 is a perspective view of the square spiral wrap bed 302. The stretched ribbon sheets 314 are disposed in parallel layers 322. Each layer 322 is generally rectangular. Each layer 322 has an unstretched sheet length less than the layer length dimension. The spacers 316 between the sheets 314 define substantially parallel fluid flow channels 318. Each fluid flow channel 318 has a first rectangular face 320 which is adjacent a first layer 314 and a second rectangular face 330 adjacent a second opposite layer 314'. The double headed arrows indicate the reciprocating air flow direction through the flow channels 318 in each of the four separate sections 360, 362, 364, 366 and over the stretched elastomer sheets 314. Housing 304 and solid or capped core 306 force the fluid flow to go through the flow channels 318 formed by the adjacent elastomeric sheets 314 and spacers 316. The flow channels 318 in this case take the form of truncated rectangular based pyramids. FIG. 12 ' shows the detail of preferred angle shaped spacer 316;

FIG. 9 shows HME assembly 300, in which, a square spiral-wrap bed 302 is inserted into a housing 304. Housing 304 is in two pieces 350 and 352, respectively. Square bed 302 is slipped into one piece 350. The other piece 352 is slipped over the protruding half of the bed 302. The two halves 350, 352 of the housing 304 are then joined at the separation line or seam 354. As best shown in FIGS. 9 and 10, the housing 304 has two tubular openings 370 and 372, respectively. One tubular opening mates with the end of the endotracheal tube, and the other tubular opening mates with a Y-connector which connects to the ventilating machine.

FIG. 10 is a top plan view showing the housing 304 of device 300. Section line 1—1 is drawn through the housing separation line 354. The bottom view is identical to the top view.

Figure 11:
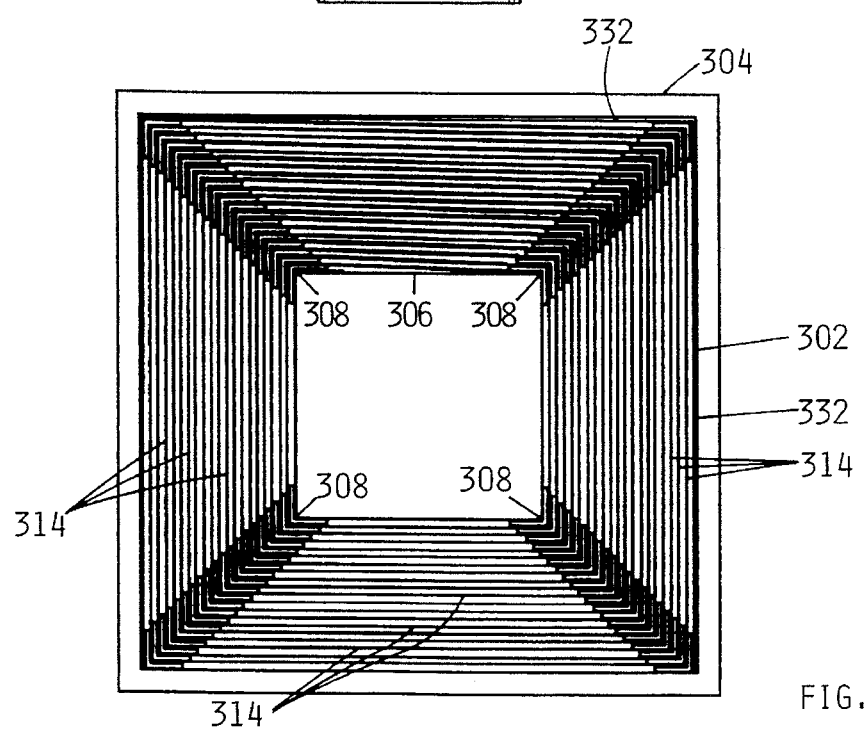
FIG. 11 is a cross sectional view of the embodiment of the FIG. 9 taken along section line 1—1 as shown in FIG. 10 illustrating the elastomer bed HME utilizing a spiral wrap assembly with four spacers per turn, showing the elastomeric sheets, spacers and flow channels.

FIG. 11 is a cross sectional view of device 300 taken along section line 1—1 as shown in FIG. 10. The bed 302 utilizing a spiral wrap assembly with four spacers per turn is shown including the sheets 314, spacers 316 and flow channels 318. The square spiral-wrap bed 302 fits snugly in the housing 304 so that air flow can not go around the outside of the bed 302. The walls of the housing are dimensioned to allow a snug fit between the exterior of the bed 302 and the interior walls of the housing 304. Thus, air gaps 332 between the interior housing wall and the outermost surface of the square wound elastomer regenerator 302 are minimal so as to prevent flow through the air gap.

The square core 306 is solid to prevent fluid flow from going through it and bypassing the elastomer sheet flow channels 318. The square core 306 can be tubular, for reduced weight. Preferably, acrylic square tubing is used which has 1/16 inch wall thickness. When tubing is used, however, the square tubular opening must be closed or capped to prevent fluid flow bypassing the elastomer sheet channels 318. Inserts, e.g., styrofoam inserts, are suitably used to block core 306.

Figure 13:
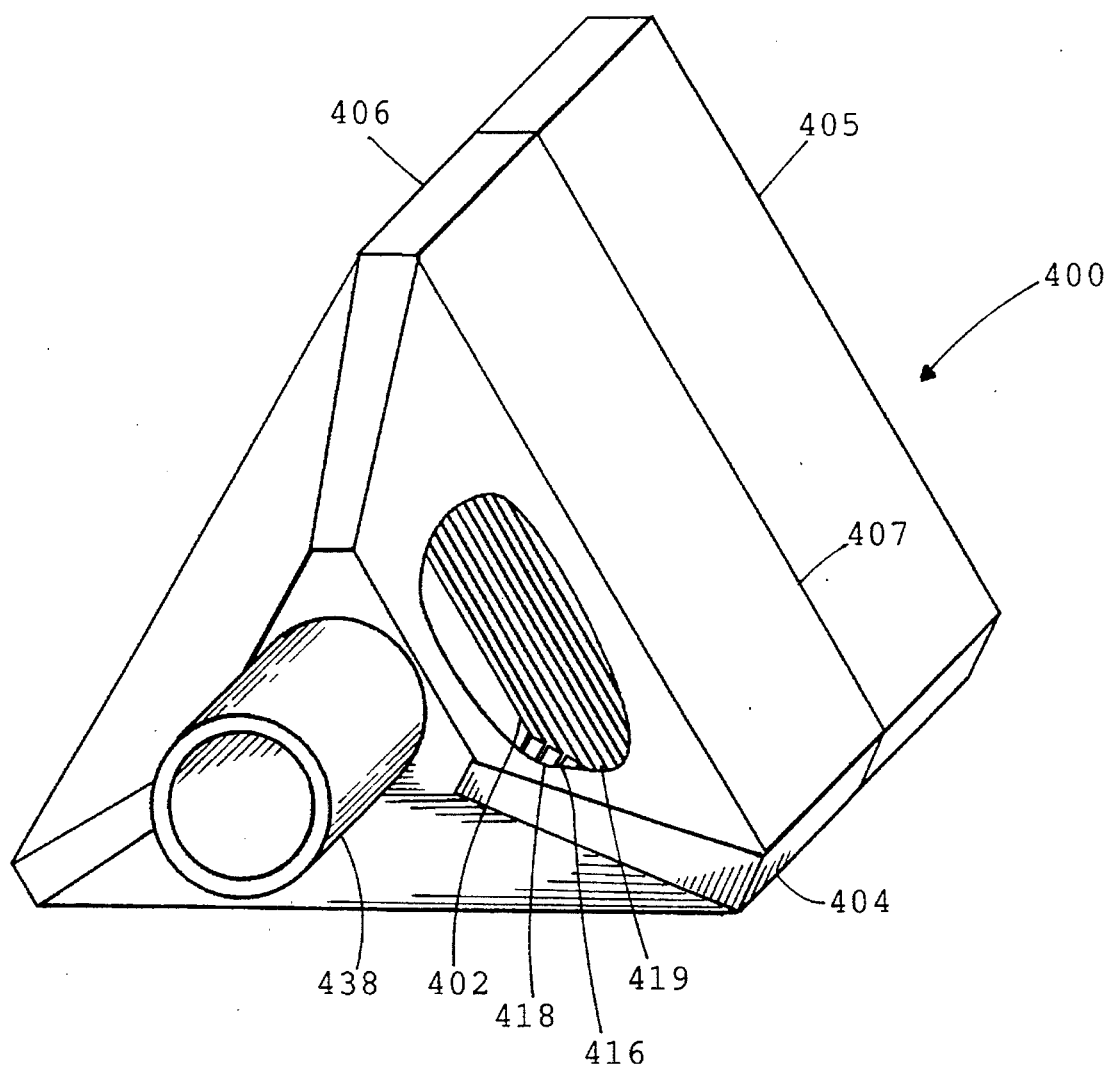
FIG. 13 is a perspective view of yet another embodiment of the device of the present invention showing a elastomer bed heat and moisture exchanger for medical ventilation in a housing; the cut away lines in the housing show the detail of the spacers, the flow channels and the elastomer sheets of the elastomer bed HME.

FIGS. 13–18 show yet another embodiment of the spiral wrap bed HME device of the present invention. FIG. 13 is a perspective view of a device 400 of the present invention showing a triangular spiral wrap bed 402 for medical ventilation in a housing 404. The cut away lines in the housing 404 show spacers 418, flow channels 419 and sheets 416 of the bed 402.

Figure 14:
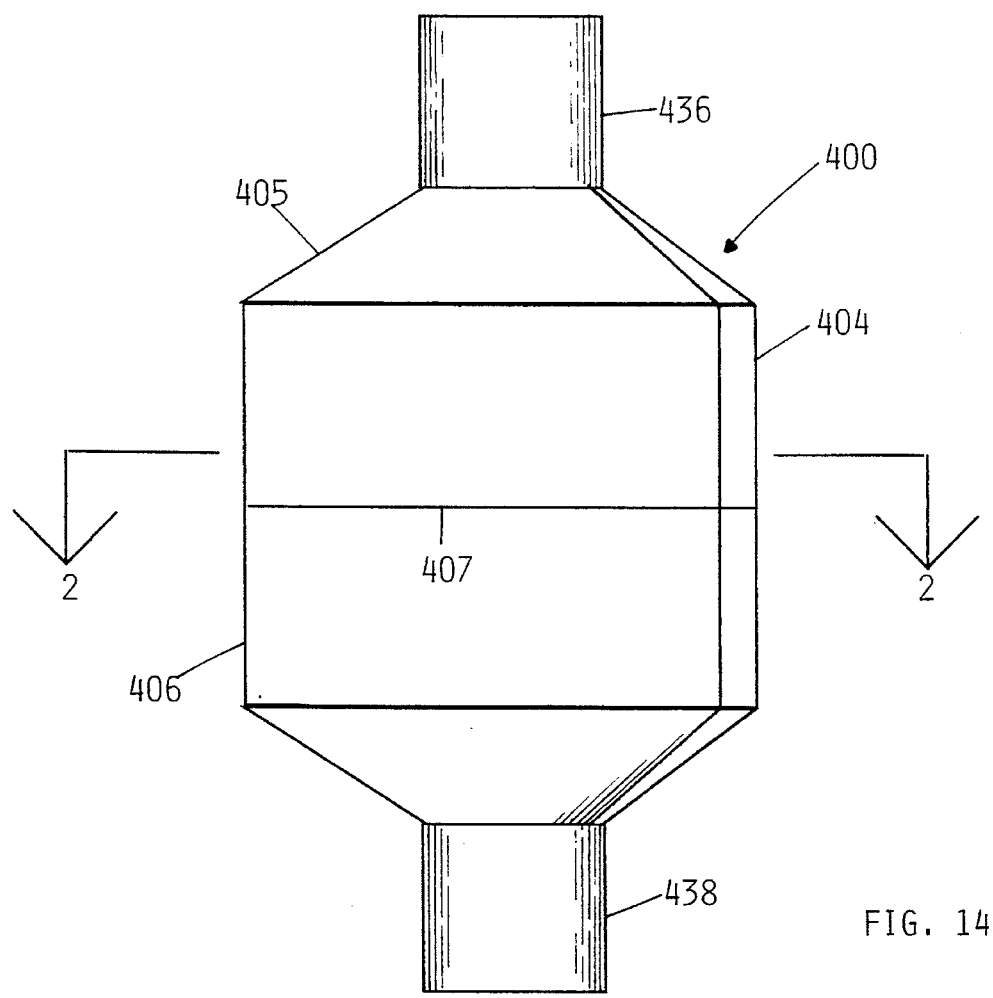
FIG. 14 is a top view of the embodiment of FIG. 13 with the device rotated having cross section line 2—2 taken through the housing and the elastomer bed HME.

FIG. 14 is a top view of device 400 with the device 400 rotated. Cross section line 2—2 is taken through housing 404 and the bed 402.

Figure 15:
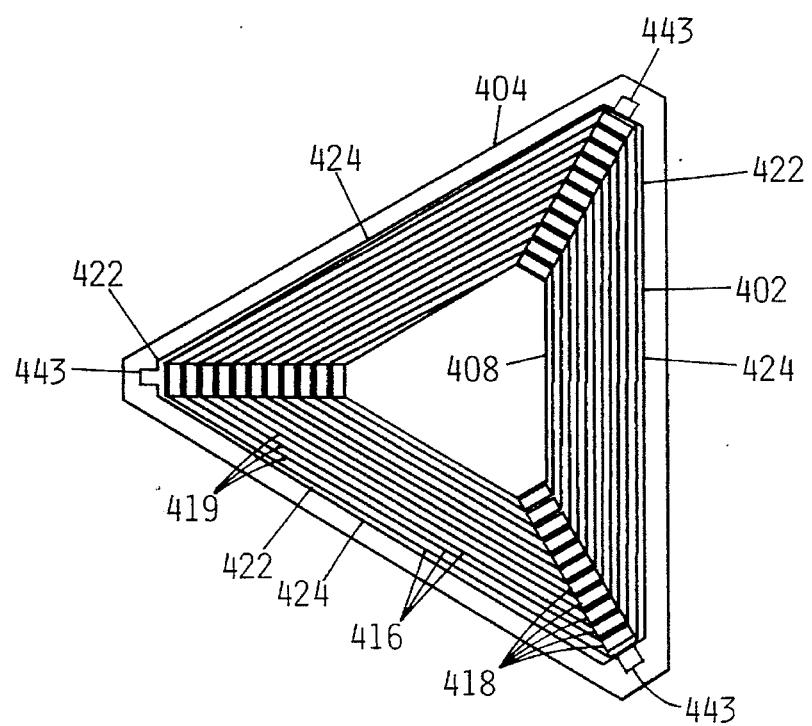
FIG. 15 is a cross-sectional view of the embodiment of FIG. 13 taken through cross section line 2—2 of FIG. 14 illustrating the components of spacers, flow channels, and elastomer sheets.

FIG. 15 is a cross sectional view of the embodiment of FIG. 13 taken through cross section line 2—2 of FIG. 14, and illustrating the component spacers 418, flow channels 419, and sheets 416.

Figure 16:
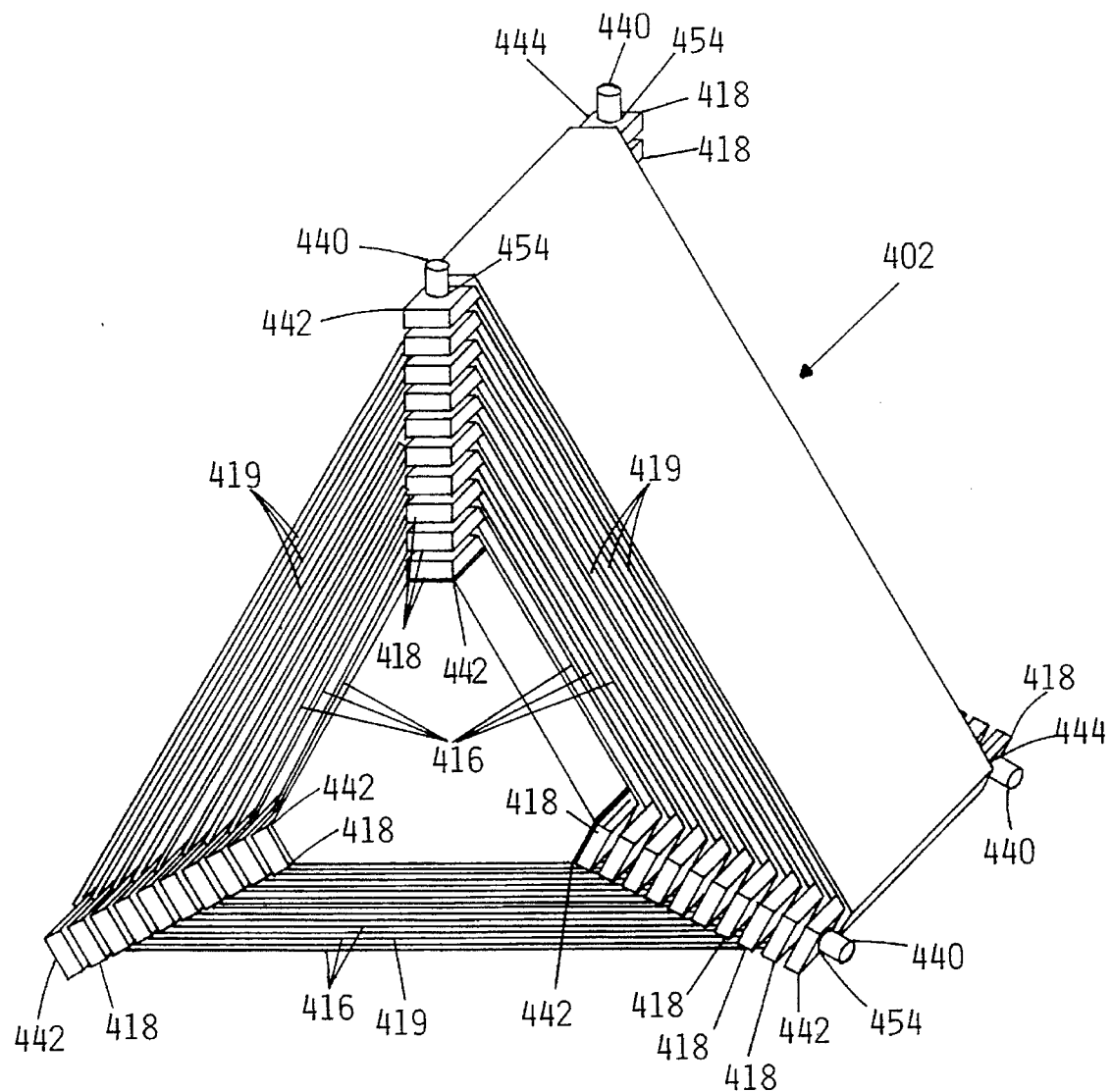
FIG. 16 is a perspective view of the triangular wrapped elastomer bed HME of FIG. 13 illustrating the flat spacers and pins for locating and securing the stack of spacers; the elastomer sheets are secured by the spacers.

FIG. 16 is an enlarged perspective view of the triangular spiral wrapped bed 402 of FIG. 13 illustrating flat spacers 418 and pins 440 for locating and securing a stack of spacers 418.

Figure 18:
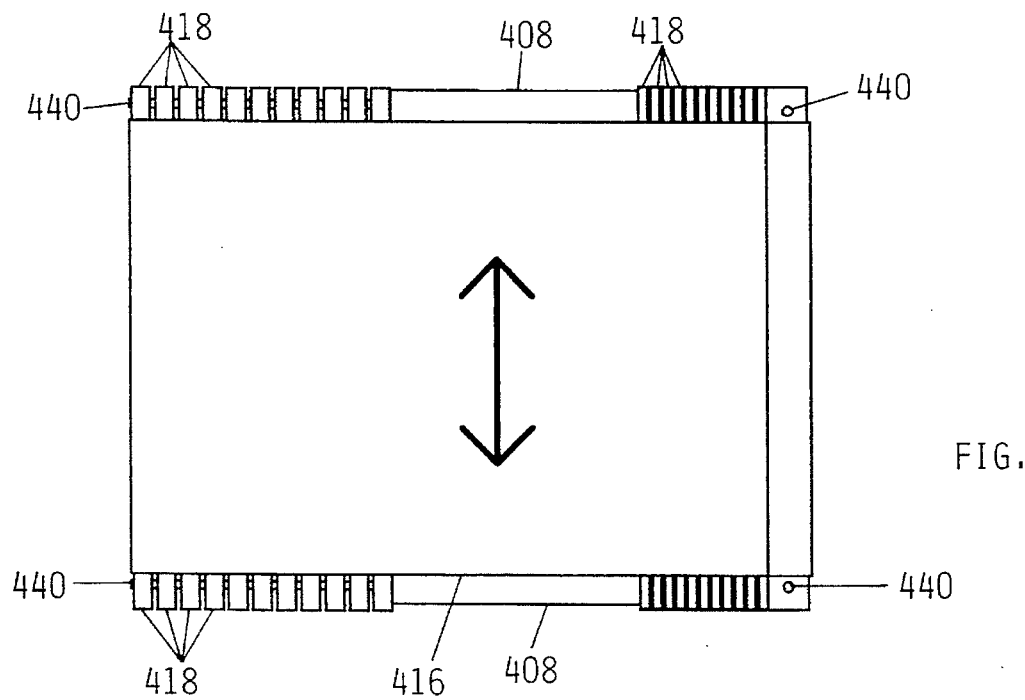
FIG. 18 is a top view of the HME bed as shown in FIG. 17, showing the direction of flow of air through the flow channels.
Figure 17:
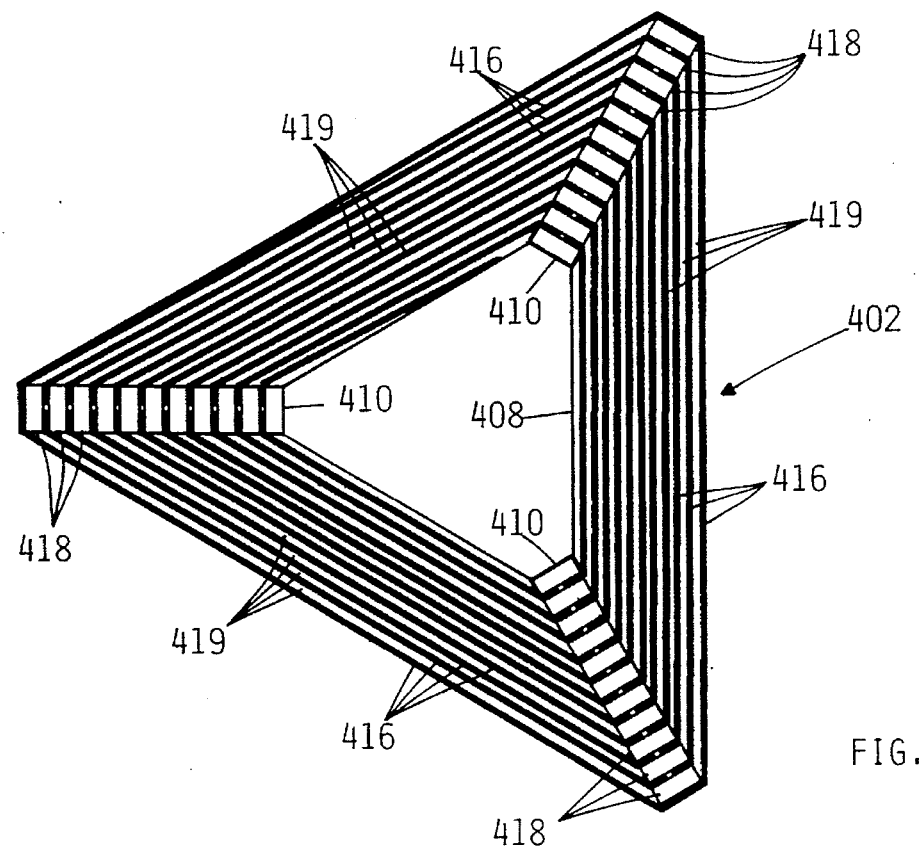
FIG. 17 is an enlarged view of only the elastomer bed HME as shown in FIG. 15.

FIG. 17 is an enlarged view of bed 402 only as shown in FIG. 15. FIG. 18 is a top view of bed 402 as shown in FIG. 17, showing the direction of flow of air through flow channels 419.

A triangular spiral wound regenerator bed 402 suitable for use as heat and moisture exchanger is suitably prepared as previously discussed for the square spiral wrap bed 302. In this instance, a triangular core 408 is rotated about a shaft (not shown) while wheels (not shown) maintain a constant tension in a ribbon 412 as it feeds the ribbon. Ribbon 412 in tension is shown by reference numeral 416. Spacers 418 are added at a specific location along ribbon 412. Spacers 418 are thus disposed at uniformly spaced corners 410 of core 408. If glue is added to both sides of spacer 418 prior to contact with the ribbon 412, the spiral wound bed 402 will not unravel when the ribbon 412 is cut.

FIG. 16 shows an alternate embodiment where instead of gluing the spacers, flat spacers 418 are used and pins 440 are used at either end 442, 444 of the spacer stack to align the spacers 418 and to lock the spacers in place. The method of creating this embodiment is explained hereinafter in conjunction with FIG. 19.

FIG. 13 shows a perspective view of the triangular spiral wrap bed 402 in its housing 404. Housing is in two pieces 405 and 406, respectively. The triangular bed 402 is slipped into one piece. The other piece is slipped over the protruding half of the triangular bed 402. The two halves 405, 406 of the housing 404 are then joined at the separation line or seam 407.

Triangular housing 404 is placed around the triangular spiral wound bed 402 after the winding process. As best shown on FIG. 15, the gap 422 between the exterior most ribbon surface and the side walls of the housing is neglible so as to prevent flow through the gap 422. This is accomplished by dimensioning the interior surfaces of triangular housing 404 side walls 424 to be slightly larger than the outermost surface of the triangular spiral wrap bed 402. Each half of the housing has a tubular flow connector. Tubular flow connector 436 penetrates a sidewall of housing half 405 creating a passageway for air flow to the ventilator. Tubular flow connector 438 penetrates a sidewall of housing half 406 to create an air passageway for air flow to the patient's endotracheal tube. The housing 404 and solid core 408 force the respiratory air flow to go through the fluid flow channels 419 formed by adjacent elastomer sheets 416 and spacers 418. Channels 419, in this case, take the shape of rectangular based truncated pyramids. FIG. 15 also shows the interior of the housing having notched portions 443 therein to accommodate the pins 440.

Figure 19:
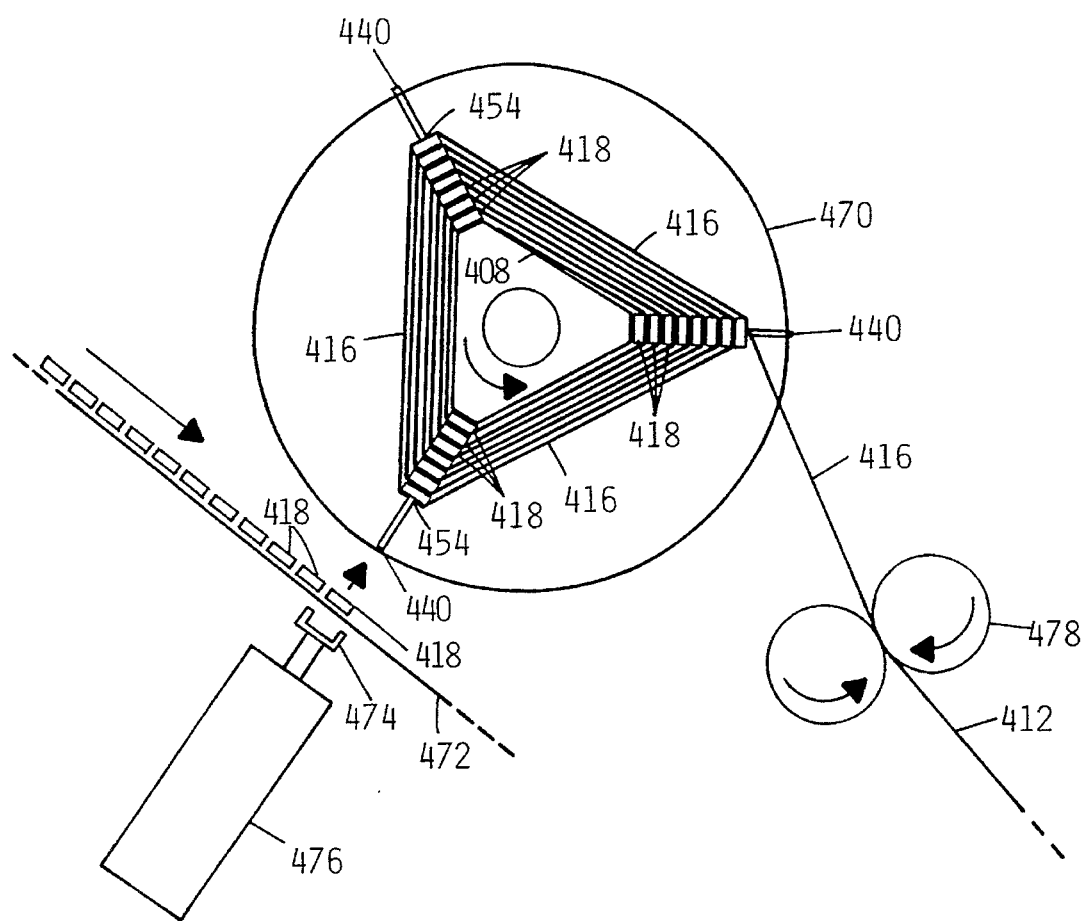
FIG. 19 illustrates a method of preparing the triangular spiral wrap elastomer bed HME of FIG. 16.

FIG. 19 illustrates another method of manufacturing the triangular spiral wrap bed 402 as shown in FIG. 16. The core 408, with the pins 440 in place, is fastened to a rotating table 470 which rotates in an indexed fashion, rotating a third of a turn, then stopping, in a repetitive fashion. The ribbon 412 is fed through tension rollers 478 under constant tension. The ribbon under tension is shown as 416. Initially, the welder (not shown) or gluer (not shown) fastens ribbon 412 to the solid core 408. The core 408 then rotates. Every time the core 408 stops, a spacer 418, with the holes 454 punched at either end, is removed from a conveyer belt 472 by the transfer head 474 on the transfer actuator 476 and forced over pins 440 in the direction shown into position on top of the growing elastomer bed 402. When the transfer actuator 476 withdraws the transfer head 474, the conveyer 472 steps forward one position. When the required number of turns have occurred, the welder or gluer fastens ribbon 416 to the layer below, the ribbon 416 is cut and the triangular bed 402 is removed to be placed into the housing 404.

Figure 20:
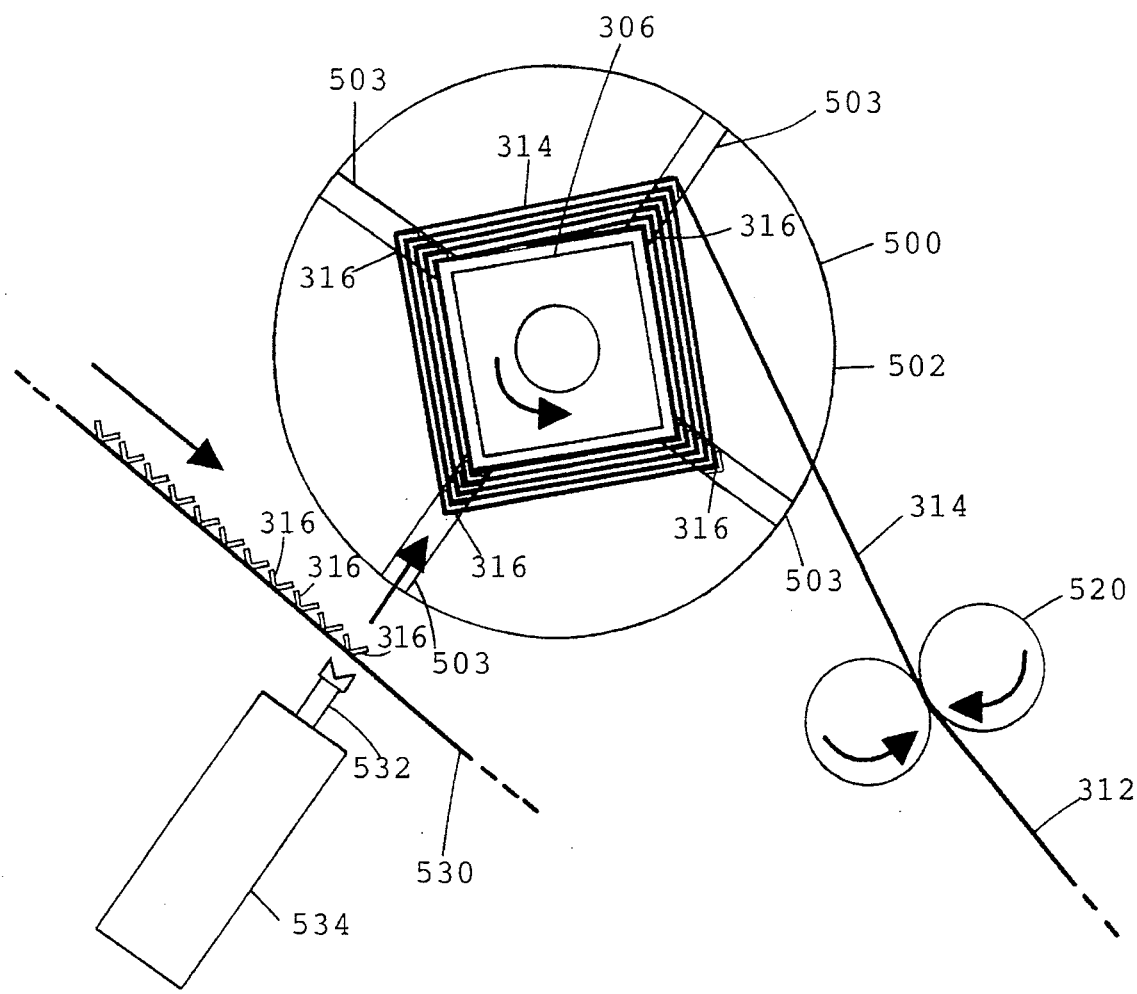
FIG. 20 illustrates another method preparing a square spiral wrap elastomer bed HME of FIG. 12.

FIG. 20 illustrates still another method of manufacturing the square spiral wrap bed 302 as shown in FIG. 12. The winding fixture 500 consists of a rotating table 502 which rotates in a indexed fashion, rotating a quarter of a turn, then stopping, in a repetitive fashion. Rectangular slots 503 in the fixture 500 are milled into the fixture 500 at 90 degree angles radially from the corners of the plastic square core 306 to help guide the right angle spacers 316 as shown also in FIG. 12'. A plastic square core 306 is placed on the fixture 500 and ribbon 314 is attached to the plastic square core 306. Ribbon 314 is fed under constant tension maintained by tensioning rollers 520. The fixture 500 with the core 306 rotates in the direction shown. Every time the core 306 stops, a spacer 316 is removed from the conveyor belt 530 and forced by the transfer head 532 on the transfer actuator 534 and forced in the direction shown into the position on the top of the growing bed 302. When the actuator 534 withdraws the transfer head 532, the conveyor 530 with spacers 316 steps forward one position. When the required number of turns have occurred, a welder (not shown) or gluer (not shown) fastens the elastomer ribbon 314 to the layer below. The ribbon is cut and the square bed 302 is removed to be placed in the housing 304.

Practical embodiments of both the square and triangular elastomer bed HME have been constructed. It has been found that the ribbon, particularly an elastic ribbon, has a tendency to develop ripples perpendicular to the direction of tension or stretch. The dimension of these ripples can easily be greater than the sheet spacing, and must, therefore, be avoided. In the semi-automated assembly in accordance with the present invention, ripples, when they occur, can be removed by spreading the sheet, e.g., elastomer sheet, lengthwise along the spacer below it, prior to placing the next spacer on top. This can be accomplished by spreading the elastomer with one's fingers.

It is noted that if angled spacers are used, and they do not nest well, forces cause the spacers to partially flatten so that the elastomer and spacer are no longer parallel at the point where the elastomer leaves the spacer. It was also found that if the spacers are not very uniform and stacked with good alignment, nonuniform sheet spacing will result. In the case where flat spacers are used, the spacers must be very uniform and precisely aligned to maintain uniform elastomer sheet spacing.

The tensioned sheets in accordance with the present invention are in a state of high potential energy. It has been found that there is a tendency for the entire wrap to twist relative to the core such that the spacer stacks collapse. In the case of flat spacers inserted over rods, the rods provide the necessary stability. In the case of nesting spacers, fixing the tubular core with respect to the housing will prevent this twisting motion. Fixing the core with respect to the outer housing is straightforward.

Figure 21:
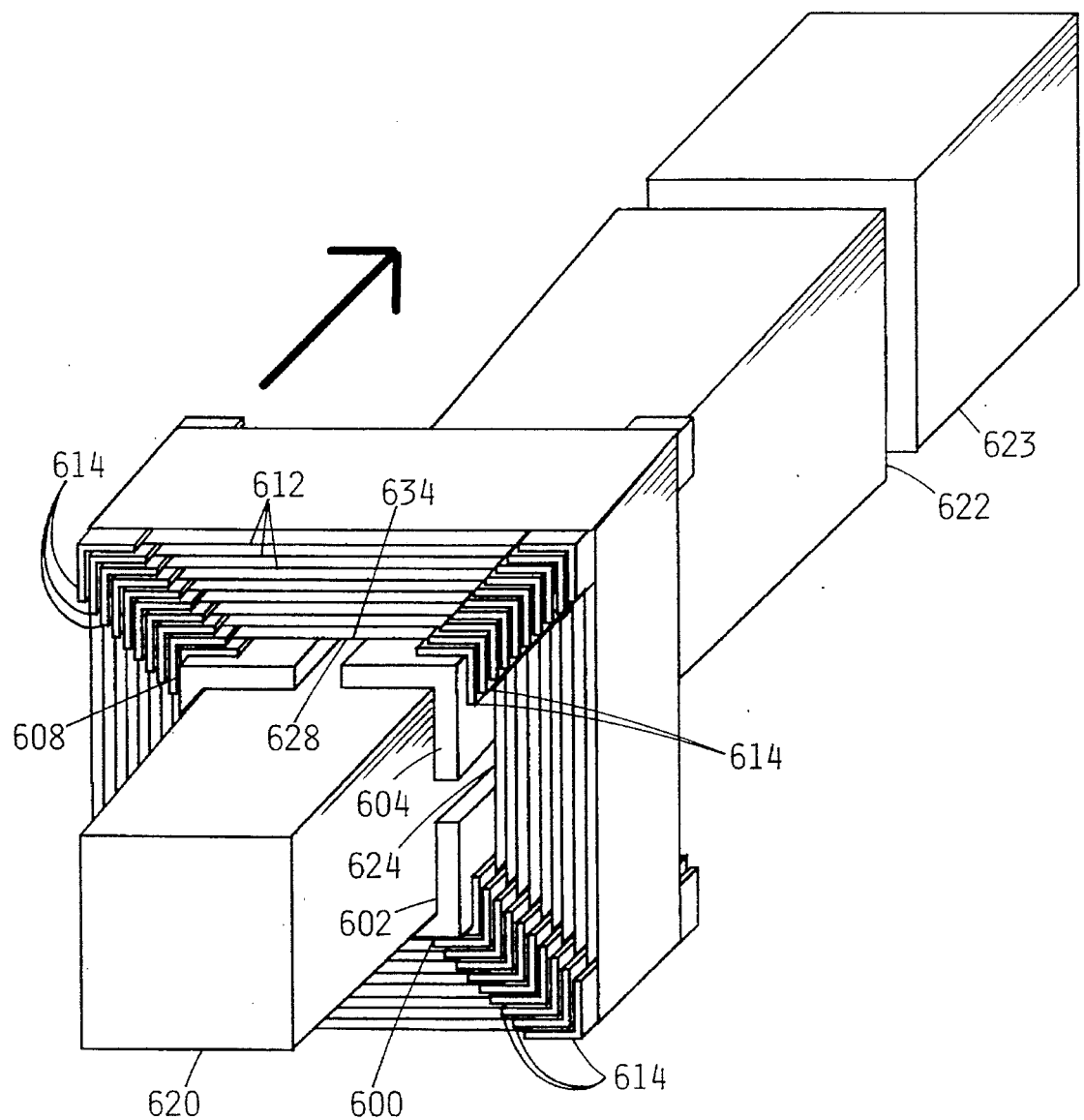
FIG. 21 illustrates a method of stretching the square spiral wrap core of FIG. 12 after wrapping.
Figure 22:
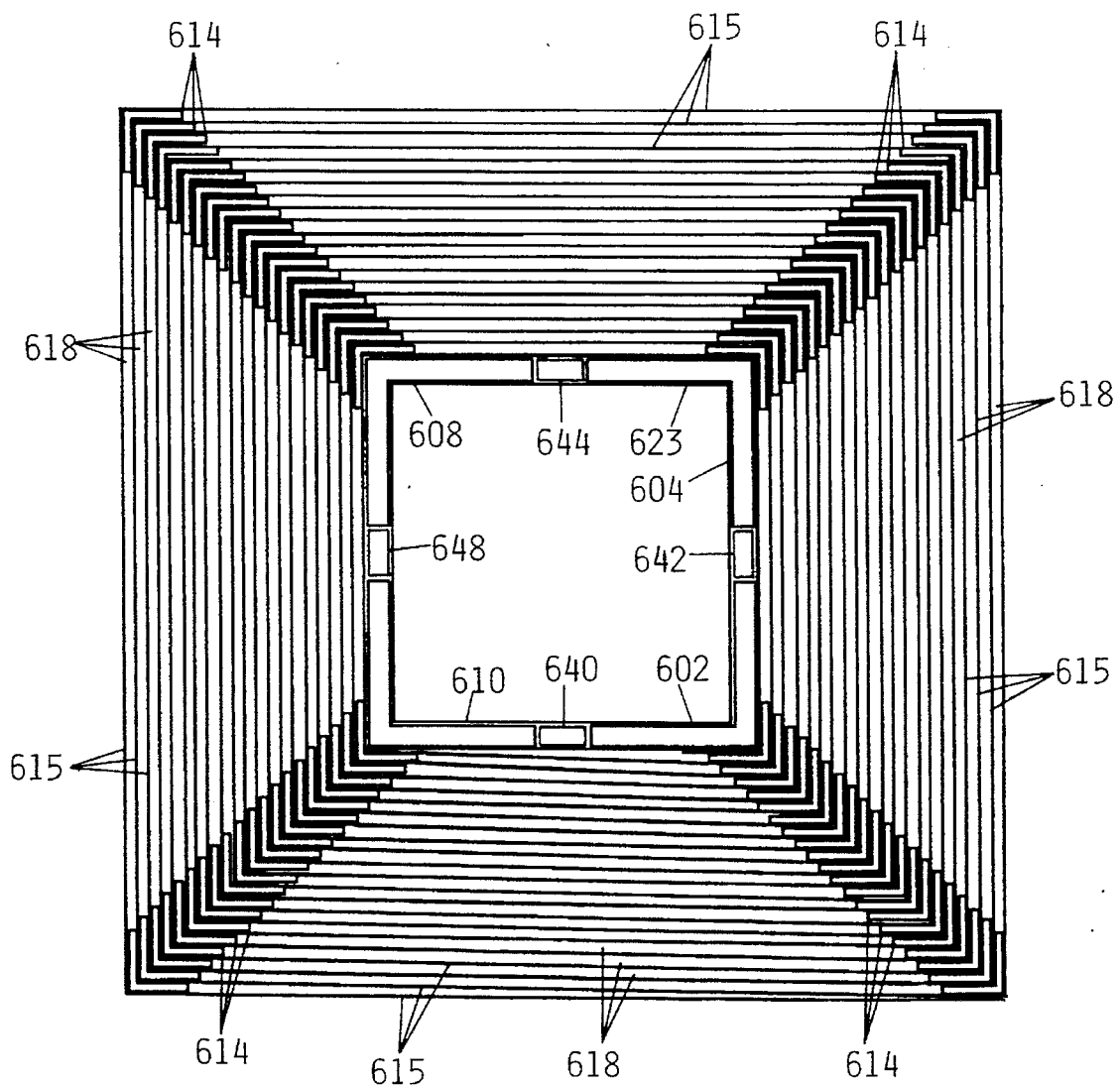
FIG. 22 illustrates a cross sectional view of the square spiral wrap segmented core embodiment of FIG. 21.

A method of manufacturing the spiral wrap, as shown in FIG. 21, helps eliminate some of the above problems. In this method, a polygonal shaped spiral wrap bed is constructed and the core used is segmented. For example, in the case of a square core 600, the core is segmented into four pieces 602, 604, 608 and 610, respectively, each piece having the shape of a right angle L-shaped rod. The spiral wrap is performed on the segmented core with no stretch applied to the ribbon. The spiral wrap can be performed quickly. Any misalignment of spacers can be corrected after the spiral wrap. Since there is no tension in the ribbon 612, the spacers 614 are free to be moved. After spacers 614 have been properly aligned, the segmented core 600 is expanded and tension is introduced into the elastomer ribbon. The segmented core 600 is placed on a solid core 620. In this case, both are square in shape. The solid core 620 is a truncated square based pyramid and is tapered such that its base is larger in dimension toward the end opposite to the top end at which the segmented core is introduced. The four pieces 602, 604, 608 and 610 of the segmented core 600 are slid toward the wider end of the tapered core 620, forcing the segmented core 600 to expand and tension to be introduced into the ribbon. At the wide end 622 of the tapered core 620, a uniform square section core 623 is placed to receive the segmented core 600 and hold it permanently. There are four gaps 624, 628, 630 (not shown) and 632 (not shown), respectively, between the innermost elastomer sheet 634. As shown in FIG. 22, the uniform core 623 and the segmented core 600 are sealed to air flow with rectangular pieces of, e.g., styrofoam 640, 642, 644 and 648, respectively, sized to fit snugly. The spiral wrap bed includes spacers 614, stretched sheets 615 and fluid flow channels 618.

A significant advantage of this method of manufacture is that catenary shaped edges typically form on each of the sheets. This manufacture method produces a very flat stable sheet with no ripples in the direction of stretch. The catenary edges occurs because the sheets start unstretched. They are gripped tightly by the spacers before full stretch.

Figure 23:
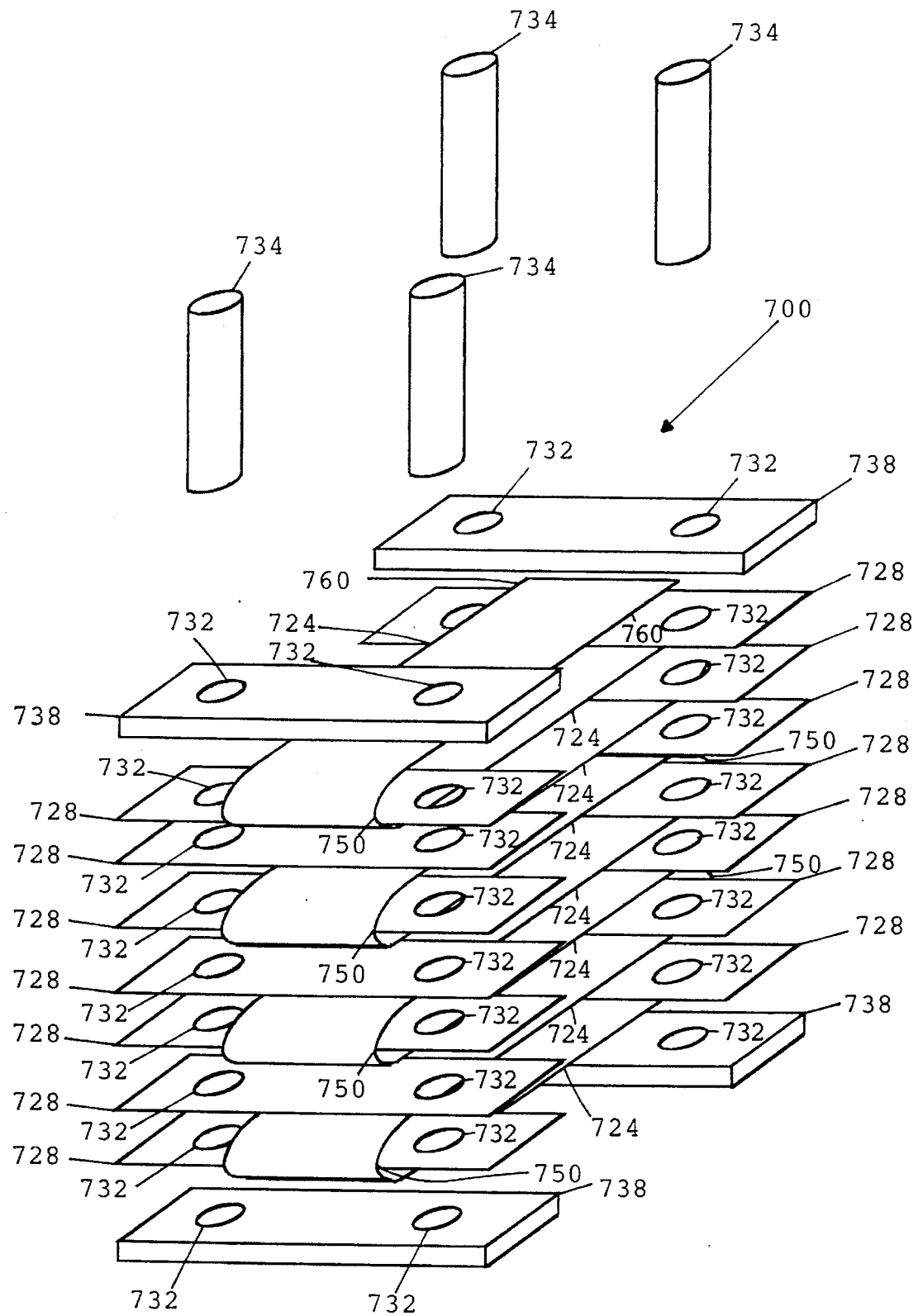
FIG. 23 is an exploded view of the elastomer sheets, spacers and rods in the "fan-fold" elastomer bed HME.

Yet another embodiment of the present invention is depicted in FIG. 23. A "fan-fold" bed eliminates the need for adhesive bonding of the spacers to the elastomer sheets or strong clamping force, yet, it provides the same sheet structure that exists in the stack-and-stretch design. FIG. 23 is an exploded view of the sheets and spacers in the fan-fold bed embodiment of the present invention. A ribbon 724 is folded back and forth in a zig-zag or "fan-fold" pattern. Spacers 728 are placed within a fold 750 and between the consecutive folds. The spacers 728 extend beyond the edges 760 of the ribbon 724 with holes 732 to accept rods 734. Rectangular end blocks 738 provide sufficient restraint to hold the spacers 728 flat. The spacers 728 within the folds 750 provide the necessary structural strength to react to the forces of the tensioned sheets 724.

After the fan fold stack 700 is assembled, the "fan-fold" HME 700 is handled in the same manner as the stack-and-stretch design previously explained herein.

The spiral wrap bed HME design is more readily made lightweight. While weight is not a key performance parameter such as moisture retention, dead volume, and pressure drop, it is relevant. More care must be taken with a heavy HME to prevent accidental dislodging of the tracheal tube.

The stack and stretch bed HME can be scaled down to the size required for infant or neo-natal patients. In these cases, dead volume as small as about three cubic centimeters are required. The spiral wrap bed HME can not practically be scaled down to that size.

In the stack and stretch bed HME, catenary like edges form on each sheet after stretch. This occurs because each sheet is grasped along opposite edges with the sheet relaxed. Tensioning causes the sheet to become thinner in both directions perpendicular to the stretch.

In order to further optimize the performance of the bed HME, other inventive techniques may be used.

The preferred embodiment uses the bed regenerator with substantially rectangular laminar flow channels. The heat capacity of the bed in accordance with the present invention can be increased by using a sheet material that absorbs water. As used herein, moisture absorbing and desorbing properties refer to water absorption of at least 15% of its weight when immersed in water. The preferred material is a hygroscopic elastomer which can directly absorb and desorb most of the 44 mg of water per L of patient breath. Further, if the hygroscopic material absorbs water and thereby adds to the heat capacity of the bed, good performance can be obtained with less material.

Such a class of elastomeric materials are elastomeric hydrogels and can consist of elastomeric polymers into which a moisture absorbing polymer has been crosslinked. For example, a polyurethane elastomer can be made by linking polyethylene glycol as a portion of the soft segment, and another material as the hard segment, forming an elastomeric polymer network which absorbs water, but is not itself soluble in water. An example of such an elastomer is TPH RL 146-37 (available from Tyndale-Plains Hunter, Ringoes, N.J.) which is soluble in alcohol, but not soluble in water and which can absorb several times its weight in water.

A second method in accordance with the present invention to incorporate a hygroscopic material into the bed is to make a composite elastomer film with a core material (chosen for its tensile strength, tear resistance, elastomeric properties and manufacturability) and coated with a hygroscopic elastomer. This has the advantage of allowing separate variation of the physical properties of the core bed material and the hygroscopic properties of the coating. An example of this construction is use of a polyurethane film (such as Morton International Morthane PB363-200 [Morton International, Seabrook, N.H.]) onto which the TPH RL146-37 elastomer has been coated. A bed with the Morthane material alone performs poorly, exhibiting breakthrough (rapid change in temperature and moisture levels due to depletion of the bed heat capacity by the inhaled or exhaled breath) and poor moisture retention. Adding a thin coating of the TPH material stops breakthrough and improves moisture retention.

A third method in accordance with the present invention to incorporate a hygroscopic material is to incorporate the hygroscopic material in a polymer film which transmits water vapor and has a high moisture vapor transmission rate (e.g., 12,000 g/m²/24 hours). For example, adding a finely powdered zeolite molecular sieve to a silicon rubber elastomer prior to curing, improves the moisture absorption and desorption of the elastomer bed. The silicon rubber elastomer is normally hydrophilic, excluding water, however it does allow water vapor to penetrate into the elastomer where it is absorbed by the molecular sieve. Using this technique, materials such as fine inorganic powders not normally used in HMEs can be used without concern about surface adhesives. The elastomer matrix acts as both a binder for the powder and as a membrane through which water vapor can pass.

Other suitable hygroscopic material includes, but is not limited to, hygroscopic salts such as LiCl, $CaCl_2$; hygroscopic polymers such as, polyacrylic acid, polyvinyl pyrrolidone, polyvinyl alcohol, or other hygroscopic polymers; or other liquid hygroscopic materials such as glycol, polyethylene glycol or glycerin.

A combination of several of the above techniques can also lead to additional advantages. The preferred elastomer bed embodiment uses a substrate or base elastomer of an elastomer chosen for its physical characteristics coated with a mixture consisting of an inorganic hygroscopic material and a hygroscopic elastomer having both a high moisture vapor transmission rate and high moisture absorption. The substrate is chosen for adequate tensile strength and tear resistance so that the elastomer tension can be adjusted to prevent water from drawing two adjacent sheets together. Any water which enters the bed is drawn up between the sheets by capillary action and can be readily drained, or blown out. This also allows the bed to be cleaned in a cleaning and disinfecting solution for patient reuse. The substrate is then coated with a mixture of inorganic hygroscopic material imbedded in a matrix of moisture absorbing and water vapor transmitting elastomer. The inorganic material is chosen to absorb water at low relative humidity, such as will occur toward the ventilator end of an HME. The high moisture vapor transmission rate of the elastomer is needed to allow water vapor to reach the inorganic material at the dry end. The ventilator end of the HME is dried by the inhaled dry medical gases which pass over it. In turn, it adsorbs water and reduces humidity of the exhaled air from the patient. The patient end of the HME must adsorb and desorb the most moisture, since saturated air at 37° C. contains a large amount of moisture. The hygroscopic elastomer is chosen so that it swells by absorbing water at the hot, moist, patient end, adding to the bed heat capacity where it is most needed, and increasing the rate of water adsorption and desorption.

The coating described above can be used to improve the hygroscopic performance and heat capacity of alternate laminar flow channel regenerative devices. Laminar flow channels can be constructed of plastic as in U.S. Pat. No. 4,875,520 or paper as in U.S. Pat. No. 5,010,594 and U.S. Pat. No. 4,594,860, or folded or waved non-air permeable strips as described in U.S. Pat. No. 5,320,096. Prior to construction, the materials can be coated with a mixture of inorganic hygroscopic material imbedded in a matrix of moisture absorbing and water vapor transmitting elastomer.

The coating process can be per/brined using a number of common processes. One process dissolves the moisture absorbing and water vapor transmitting elastomer in a solvent mixed together in the proper ratio with the inorganic hygroscopic material. Solvent-based coating techniques commonly employed in the film conversion industry, such as transfer printing, dipping, air-knife, or Meyer rod coating, can be used to coat a paper, plastic, elastomer, or thin metal film. Alternately, a pre-polymer mixture can be coated and heat or solution cured after coating. Further, a thermoplastic elastomer pre-mixed with the inorganic hygroscopic material can be coated by heating the elastomer to an elevated processing temperature, melting the material, and by extruding the melted material from an extrusion die onto the substrate film of paper, plastic, elastomer, or thin metal. Some substrates, such as plastic or elastomer film, may be co-extruded at the same time.

Having described the invention in general, the following are specific examples of the present invention. The examples are to be construed as merely illustrative, and not limitative of the remainder of the disclosure in any way whatsoever.

EXAMPLE 1

A bed HME in accordance with the present invention using elastomer materials was constructed. A base elastomer or substrate was coated with a hygroscopic elastomer selected for its moisture absorbing and desorbing properties. Specifically, both sides of a rectangular piece of 0.008" thick Deerfield Urethane PS8420F (Deerfield Urethane, Inc. South Deerfield, Mass.) polyester material of approximately 18" by 24" size ruled in 3" wide columns (which served as coating guidelines) were coated. The coating material was a hydrophilic urethane prepared by dissolving 10 grams of TPH RL 145-18 polyethylene oxide polyurethane polymer (available from Tyndale-Plains Hunter, Ringoes, N.J.) in 100 mL ethyl alcohol, which produced a syrupy liquid which was coated on the base elastomer using a Meyer rod. A Meyer rod of 5/16" diameter wrapped with 22 gauge wire was used to spread the solvent and urethane mixture and produced a 0.001" thick coating of elastomer after the solvent evaporated.

When both sides were coated and dried, the elastomer was cut into 45 pieces of equal area with four holes punched in each piece, two on each end. Eighty eight spacers (of polyvinyl chloride (PVC)) were constructed and stacked with the elastomer pieces using the stack and stretch method and threaded bolts. The bolts provided the clamping force to secure the elastomer prior to stretching. A stretching fixture of four square Lexan® rods drilled with holes matching the spacers in one direction and with holes separated by threaded rod in the other direction was used to stretch the elastomer in the center of the bed from an unstretched length of 1½" to a stretched length of 2". The stretched bed was then fitted with end caps having 15 and 22 millimeter standard HME fittings. The bed had the following characteristics:

| | |
|---|---|
| Elastomer unstretched thickness with coating | 0.010" |
| Spacer thickness | 0.015" |
| Bed width | 1.13" |
| Bed height (stretched) | 2.0" |
| Bed length | 2.0" |
| Bed porosity (pore volume/total volume) | 64% |

After stretching, the channels were 0.016 in. (inches) wide and extend 2.0 in. and 2.0 in. in the two directions. The channels were unobstructed in any way. There were approximately 44 channels in the bed. The channels in the elastomer regenerator were essentially rectangular in shape. The aspect ratio for a channel with a height of 2 in. and a width of 0.016 in. is 125:1, which provides virtually the same performance as infinite parallel channels.

It is noted that prior art regenerator wheels, for room temperature ventilation, often use many layers of fine aluminum wire mesh stacked in the direction of flow. Pressure drop can be relatively high for this type of matrix. The use of corrugated foil, stacked perpendicular to the direction of flow, has alleviated the pressure drop problems, and results in a structure resembling a small pore honeycomb. The channels, however, resemble rounded triangles. The parallel channels of the bed of the present invention have a significantly better heat transfer to pressure drop ratio than such corrugated face structures. The matrix in accordance with the present invention can have significantly higher porosity than the existing technologies. This can be an advantage if the matrix material has a high heat capacity per unit volume, such as about 2 J/cm$^3$°C. Elastomers have such a high heat capacity per unit volume.

The contribution of absorbed water to increasing the heat capacity of the elastomer bed was estimated. The selected elastomer absorbs about 500% of its weight if immersed in water. In operation, the actual absorption may have been less than this amount. Given the physical characteristics of the bed and assuming that the absorbed water adds heat capacity of about 4.22 J/g°C. to the elastomer, the calculated heat capacity gain of the elastomer bed was 211%.

EXAMPLE 2

An elastomer bed HME was constructed with a base elastomer and coated with a hygroscopic elastomer selected for both its moisture vapor transmission characteristics and its moisture absorbing and desorbing properties. A separate hygroscopic material was blended in with the hygroscopic elastomer.

Specifically, a bed was constructed in the same manner as Example 1, except that the hydrophilic coating was made of 5 grams of TPH RL 145-18 polyethylene oxide polyurethane polymer (available from Tyndale-Plains Hunter, Ringoes, N.J.) dissolved in 100 mL ethyl alcohol to which 15 grams of Utikon Silica Gel E (Zeochem, Louisville, Ky.), 30 micron powder was added. Frequent stirring dispersed and suspended the inorganic material in the mixture. The resulting bed had the same physical characteristics as the bed in Example 1.

The contribution of absorbed water to increasing the heat capacity of the elastomer bed was estimated. The selected hygroscopic elastomer absorbs about 500% of its weight if immersed in water. In operation, the actual absorption may have been less than this amount. However, since silica gel was mixed in at a 3 to 1 ratio, only one fourth of the coating was moisture absorbing elastomer. Given the physical characteristics of the bed and assuming that the absorbed water adds heat capacity of about 4.22 J/g°C. to the elastomer, the calculated heat capacity gain of the elastomer bed was 53%.

The beds of Examples 1 and 2 were tested. The test apparatus consists of a weather balloon filled with dry air (dried by a molecular sieve desiccant), a Y-connector with one way valves, an outlet tube, and temperature and humidity probes. The patient is at one end of the HME. The other end of the HME is connected to the Y-connector. The air in the balloon is measured for temperature and moisture content before the test and after the test. An adult breathes dry air from the balloon through the HME at the patient end while the one way valve to the tube is closed. Then the one way valve to the balloon is closed and the one way valve to the tube is opened. The patient exhales his moist breath through the HME through the open one way valve into the tube. The one way valve to the tube is then closed. These steps are repeated for about 10 minutes of breathing. The temperature and relative humidity in the tube is measured before and monitored during the breath collection. The Elastomer Bed HME devices from Example 1 and Example 2 as well as an ARC® device referred to hereinbefore were tested using this apparatus. Table 5 summarizes these results.

TABLE 5

Performance of Elastomer Bed HMEs for Various Configurations and Test Conditions

| Device | Moisture Return (mg/l) | Dead Space (cc) | Pressure Drop (cm H$_2$O @ 60 lpm) |
|---|---|---|---|
| ARC Device | 32.1 | 65 | 1.5 |
| Deerfield PS8420 + TPH RL145-18 | 36.9 | 82 | 0.6 |
| Deerfield PS8420 + TPH RL145-18 + Silica Gel E | 39.4 | 82 | 0.6 |

Pressure drop was calculated but not measured because no accurate flow meter was available with which to test pressure drop. The results show that a moisture return exceeding the moisture return of the commercially available ARC® device is achievable with the present invention.

EXAMPLE 3

An elastomer bed HME was constructed with a base elastomer coated with a hygroscopic elastomer selected for both its moisture vapor transmission characteristics and its moisture absorbing and desorbing properties and a separate hygroscopic material was blended with the hygroscopic elastomer. The overall design closely matched that shown in FIGS. 3–8.

Specifically, both sides of a piece of 0.006" thick Morton Morthane PE88-224 polyurethane (from Morton International, Seabrook, N.H.) arranged in 3" wide strips (which served as coating guidelines) were coated. The coating material was a hydrophilic urethane consisting of 5 grams of TPH RL 145-18 polyethylene oxide polyurethane polymer (available from Tyndale-Plains Hunter, Ringoes, N.J.) dissolved in 100 mL ethyl alcohol to which 15 grams of Utikon Silica Gel E (Zeochem, Louisville, Ky.), 30 micron powder was added. Frequent stirring dispersed and suspended the inorganic material in the mixture. This produced a syrupy liquid which was coated on the base elastomer using a Meyer rod. A Meyer rod of 5/16" diameter wrapped with 22 gauge wire was used to spread solvent and the mixture and produced a 0.001" thick coating of elastomer after the solvent evaporated.

When both sides were coated and dried, the elastomer sheet was cut into 70 equal area pieces with six holes punched in the elastomer, three on each end. A steel ruled die and arbor press were used to punch the sheets and holes in one operation. The middle hole on each end was centered in the sheet along the length dimension. 138 vinyl spacers 0.009" thick were lined with a 0.002" thick transfer adhesive (Tessa Tessafix 4985, available from Tessa, Inc., New Rochelle, N.Y.) and were punched and stacked with the elastomer pieces using the stack and stretch method and secured with threaded inserts as in FIG. 2. The inserts provided the clamping force to secure the elastomer prior to stretching. Four rectangular end pieces constructed of 1/8" Lexan® plastic were added at the ends of the bed.

A stretching fixture was constructed of four Lexan® rods drilled with holes matching the open, center hole in the stacked bed. The square rods were also drilled with holes to accept threaded rods in the direction of stretch. The elastomer in the center of the bed was stretched from an unstretched length of 1⅝" to a stretched length of 2 1/10" using the threaded rods.

The method as shown in FIG. 3 was used to stretch the bed, inserting a rod from the fixture into the unused center holes in each end of the stacked bed. The stretched bed was then fitted with end caps constructed of 1/8" acrylic and 1/16" Lexan® plastic and having 15 and 22 millimeter standard HME fittings. The bed had the following characteristics:

| | |
|---|---|
| Elastomer unstretched thickness with coating | 0.008" |
| Spacer thickness | 0.011" |
| Bed width | 1.33" |
| Bed height (stretched) | 2.1" |
| Bed length | 1.38" |

The channels in the elastomer regenerator are essentially rectangular in shape. The aspect ratio for a channel with a height of 2.1 in. and a width of 0.013 in. is 160:1, which provides virtually the same performance as infinite parallel channels.

The contribution of absorbed water to increasing the heat capacity of the elastomer bed was estimated. The selected hydrophilic elastomer absorbs about 500% of its weight if immersed in water. In operation, the actual absorption may have been less than this amount. Given the physical characteristics of the bed and assuming that the absorbed water adds heat capacity of about 4.22 J/g°C. to the elastomer, the calculated heat capacity gain of the elastomer bed was 66%.

EXAMPLE 4

An elastomer bed HME is constructed with a base elastomer coated with a hygroscopic elastomer selected for both its moisture vapor transmission characteristics and its moisture absorbing and desorbing properties. A separate hygroscopic material is blended with the hygroscopic elastomer. The bed is constructed in the same manner as Example 1, except that the base elastomer is made thinner (about 0.005"), and the coating is made thicker (about 0.0025") leading to a total base plus coating thickness of 0.010". The coating can be made thicker by using applying multiple coats using the rod from Example 1. The elastomer in the coating will absorb more water (since it is thicker), adding substantially to the heat capacity. Only the outer portion of the coating will be able to absorb and desorb the dynamic moisture required per each breath.

The contribution of absorbed water to increasing the heat capacity of the elastomer bed is estimated. The selected hydrophilic elastomer absorbs about 500% of its weight if immersed in water. In operation, the actual absorption may be less than this amount. Given the physical characteristics of the bed and assuming that the absorbed water adds heat capacity of about 4.22 J/g°C. to the elastomer, it is calculated that heat capacity gain of the elastomer bed was 528%.

EXAMPLE 5

An elastomer bed HME is constructed with a base elastomer which is hygroscopic, and absorbs and desorbs water. The hygroscopic elastomer, such as TPH 139-53 (available from Tyndale-Plains Hunter, Ringoes, N.J.) (which absorbs about 40% of its weight in water) is used in a thickness of 0.010". The elastomer is cut into 45 2" by 3" pieces with four holes punched in each piece, two on each end. Eighty eight spacers of a suitable material, such as Lexan or vinyl, are constructed, punched with holes and stacked with the elastomer pieces using the stack and stretch method and ¼" threaded bolts. The bolts provide the clamping force to secure the elastomer prior to stretching. A suitable stretching fixture is constructed and used to stretch the elastomer in the center of the bed from an unstretched length of 1½" to a stretched length of 2". The stretched bed is then fitted with suitable ends and connectors having 15 and 22 mm standard HME fittings. The bed has the following characteristics:

| | |
|---|---|
| Elastomer unstretched thickness | 0.010" |
| Spacer thickness | 0.015" |
| Bed width | 1.13" |
| Bed height (stretched) | 2.0" |
| Bed length | 2.0" |
| Bed porosity (pore volume/total volume) | 64% |

After stretching, the channels are 0.016 in. wide and extend 2.0 in. and 2.0 in. in the two directions. The channels are unobstructed in any way. There are approximately 44 channels in the bed.

The channels in the elastomer regenerator are essentially rectangular in shape. The aspect ratio for a channel with a height of 2.0 in. and a width of 0.016 in. is 125:1, which provides virtually the same performance as infinite parallel channels.

The contribution of absorbed water to increasing the heat capacity of the elastomer bed is estimated. The selected hydrophilic elastomer absorbs about 40% of its weight if immersed in water. In operation, the actual absorption may be less than this amount. Given the physical characteristics of the bed and assuming that the absorbed water adds heat capacity of about 4.22 J/g°C. to the elastomer, it is calculated that heat capacity gain of the elastomer bed is 84%.

EXAMPLE 6

An elastomer bed HME is constructed with a base elastomer which is hygroscopic and absorbs and desorbs water. The elastomer absorbs a substantial amount of water, increasing its heat capacity thereby. A very hygroscopic elastomer, such as TPH 125-31 (available from Tyndale-Plains Hunter, Ringoes, N.J.) (which absorbs about 500% of its weight in water) is used in a thickness of 0.010". The bed is constructed as in Example 5 and has the same physical characteristics as in Example 5, but with time it absorbs a substantial amount of water adding extra heat capacity to the bed.

The contribution of absorbed water to increasing the heat capacity of the elastomer bed is estimated. The selected hydrophilic elastomer absorbs about 500% of its weight if immersed in water. In operation, the actual absorption may be less than this amount. Given the physical characteristics of the bed and assuming that the absorbed water adds heat capacity of about 4.22 J/g°C. to the elastomer, it is calculated that heat capacity gain of the elastomer bed is 1055%.

EXAMPLE 7

An elastomer bed HME is constructed with a base elastomer selected for its moisture vapor transmission characteristics blended with a separate hygroscopic material forming a matrix with high heat capacity and moisture adsorption and desorption. The bed is constructed in the manner of Example 5 using a hydrophobic elastomer which readily transmits water vapor. This elastomer consists of silicon rubber loaded with 10% by weight of Zeochem 30 micron, 4A molecular sieve (Zeochem, Louisville, Ky.). The resulting silicon rubber elastomer material is Bisco EP-2026-2 (Bisco Produces, Elk Grove Village, Ill.) and is 0.010" thick. The hydrophobic elastomer provides most of the required heat capacity and, moisture vapor is adsorbed and desorbed through the elastomer by the sieve. Since so little water is absorbed by the bed in this example, the contribution of the added water to increased heat capacity is not significant.

Variations may be made to the design parameters of the present invention. Suitably flow channels have a channel width ranging from about 0.001 in. to about 0.050 in., and the stretched sheet thickness range is from about 0.0005 in. to about 0.010 in.

The device of the present invention may also be used in and, accordingly, may be dimensioned for veterinary applications.

The HME of the present invention may also be incorporated into a standard housing for use in breathing masks for medical and nonmedical applications.

In summary, the present invention provides a heat and moisture exchanger device for heating and moisturizing respiratory gases during medical artificial ventilation which utilizes the regenerator principle. The HME bed in accordance with the present invention has very fine parallel plate structure in which the sheet thickness and sheet separation can be of the order of the thickness of ordinary paper. The sheets are tensioned, preferably stretched elastomer. The elastomer may be advantageously charged or coated with hygroscopic materials to further enhance the moisture absorbing properties of the device, thereby enhancing the heat capacity and moisture return performance of the device. Compact and light weight designs are possible since the flow channel dimensions can be made smaller than competing technology.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A heat and moisture exchange device comprising a housing and a regenerative heat and moisture exchanger bed disposed in said housing;

said housing having an inlet port for communication to a first fluid source and an outlet port for communication to a second fluid source, and operatively associated with said bed for directing fluid flow through said bed;

said bed including a matrix of flat tensioned parallel sheets spaced apart to define substantially parallel flow channels therebetween, said flow channels having an aspect ratio of at least 10 to 1; said tensioned parallel sheets remaining taut and substantially unflexed during said fluid flow or a pressure drop.

2. The device of claim 1, wherein said first fluid source is a ventilation circuit and said second fluid source is a patient's respiratory system.

3. The device of claim 1, wherein the flow channels extend substantially parallel to adjacent layers of said matrix.

4. The device of claim 3, wherein said flow channels extend substantially parallel to each other.

5. The device of claim 1, wherein said matrix comprises parallel layers of flat stretched elastomer sheets.

6. The device of claim 1, wherein said sheets have a thickness of about 0.0005 inches to about 0.010 inches.

7. The device of claim 1, wherein said housing is constructed of a lightweight plastic material.

8. The device of claim 1, wherein said aspect ratio is at least 100 to 1.

9. The device of claim 1, wherein said flow channels have a channel width of about 0.001 inches to about 0.050 inches.

10. The device of claim 5, wherein said sheets are constructed of material selected from the group consisting of elastomers, natural rubber, synthetic rubber, latex, vinyl, polyethylene, plastic, polyurethane, neoprene, silicon rubber, hycar, thermoplastic rubbers, elastomer hydrogels, polyethylene oxide polyurethane polymer.

11. The device of claim 10, wherein said material is charged with a hygroscopic material selected from the group consisting of hygroscopic salts, LiCl, $CaCl_2$, hygroscopic polymers, polyacrylic acid, polyvinyl pyrrolidone, polyvinyl alcohol, liquid hygroscopic materials, glycol, polyethylene glycol, glycerin, silica gel, activated charcoal, or zeolites.

12. A heat and moisture exchange device for use in a medical artificial ventilation system comprising a housing and an elastomer regenerative heat and moisture exchanger bed disposed in said housing;

said housing having an inlet port for communication to a ventilation circuit and an outlet port for communication to a patient's respiratory system, and operatively associated with said bed for directing fluid flow through said bed;

said bed including a matrix of stretched elastomer and having flow channels therethrough; said stretched elastomer remaining taut and substantially unflexed during said fluid flow or a pressure drop.

13. The device of claim 12, wherein said matrix comprises parallel layers of stretched elastomer sheets, each said layer being generally rectangular and having a layer length dimension, each said sheet having an unstretched sheet length less than said layer length dimension; and said bed includes spacers between said sheets defining substantially parallel fluid flow channels therebetween, each said channel having a first rectangular face adjacent a first layer and a second rectangular face adjacent a second opposite layer; and locking means for locking said sheets and spacers together.

14. The device of claim 13, wherein said first rectangular face and said second rectangular face are identically dimensioned.

15. The device of claim 13, wherein said layers of elastomeric sheets comprise a ribbon of elastomer, said ribbon having a ribbon width dimension, said ribbon oriented in a parallel fold pattern creating a plurality of folds with a said spacer inserted in each of said folds, and between said folds, said spacers having a spacer length dimension greater than said ribbon width dimension, each said spacers having a pair of spacer holes therein, said spacer holes spaced at a dimension greater than said ribbon width dimension, said locking means penetrating said spacer holes.

16. The device of claim 13, wherein said bed comprises a core and said stretched elastomer is spirally wound about said core forming elastomer layers, and spacers between said layers forming said flow channels therebetween, said spacers disposed at uniformly spaced angular position about said core.

17. The device of claim 12, wherein said housing further comprises a pair of side plates for maintaining said matrix in a stretched configuration.

18. The device of claim 17, wherein said bed comprises locking means, said locking means comprising end blocks having opposing edges and wherein said side plates of said housing have opposite edges for engaging said opposing edges of said end blocks.

19. The device of claim 12, wherein the elastomer comprises a material which can be stretched at least 5% and can return to its original shape when stress is removed.

20. The device of claim 12, wherein said matrix of said stretched elastomer is hygroscopic.

21. The device of claim 12, wherein said matrix of said stretched elastomer absorbs at least 36 milligrams of water per liter of exhaled gas and desorbs at least 36 milligrams of water per liter of inhaled respiratory gas.

22. A heat and moisture exchanger bed comprising:

(a) parallel layers of flat stretched elastomer sheets, each said layer being generally rectangular and having a layer length dimension, each said sheet having an unstretched sheet length less than said layer length dimension;

(b) spacers between said sheets defining substantially parallel fluid flow channels therebetween, each said channel having a first rectangular face adjacent a first layer and a second rectangular face adjacent a second opposite layer;

(c) locking means for locking said sheets and spacers together; wherein, in use, an air stream containing water vapor is directed through said flow channels and over said sheets to effect a change in temperature and moisture content in the air stream; and wherein said stretched elastomer sheets remain taut and substantially unflexed in response to said air stream or to a pressure drop.

23. The bed of claim 22, wherein each said elastomer sheets comprises a water vapor-transmitting elastomeric matrix charged with a hygroscopic material.

24. The bed of claim 22, wherein said elastomer sheets are hygroscopic and absorb and desorb water vapor from the air stream.

25. The bed of claim 22, wherein said bed has a predetermined heat capacity and said elastomer sheets absorb an amount of water vapor sufficient to increase by at least 25% said heat capacity of said bed.

26. The bed of claim 22, each said elastomer sheets comprises a base elastomer material and a hygroscopic elastomer material coated upon said base material, said hygroscopic elastomer material capable of absorbing and desorbin water vapor.

27. The bed of claim 22, wherein each said elastomer sheet comprises a base elastomer material; and a hygroscopic, moisture transmitting elastomer material charged with a hygroscopic material and coated on said base material.

28. The bed of claim 27, wherein said elastomer material charged with said hygroscopic material absorbs an amount of said water vapor sufficient to increase by at least 25% a predetermined heat capacity of said bed.

29. An elastomer regenerative heat exchange device comprising at least one elastomer member, said elastomer member comprising a water vapor-transmitting elastomeric matrix charged with a hygroscopic material, said elastomer member being capable of absorbing and desorbing moisture.

30. The device of claim 29, further comprising a nonelastomeric member, wherein said elastomer member is coated on said nonelastomeric member.

31. The device of claim 29, wherein said matrix is uniformly charged with said hygroscopic material.

32. An elastomer regenerative heat exchange device comprising at least one elastomer member, said elastomer member comprising:

(a) a base elastomer material; and (b) a hygroscopic, water vapor-transmitting material coated on said base elastomer material, said hygroscopic, water vapor-transmitting material elastomer material comprising a hygroscopic, water vapor transmitting elastomeric matrix charged with a hygroscopic material.

33. The device of claim 32, wherein said device has a predetermined heat capacity and said hygroscopic, water vapor transmitting material absorbs an amount of said water vapor sufficient to increase by at least 25% said heat capacity of said device.

34. The device of claim 1, wherein said sheets have a tensile strength greater than 650 psi, a tear resistance greater than about 70 pounds per inch, and a specific heat capacity of about 2 Joules per gram per °C.

35. The device of claim 22, wherein said sheets have a tensile strength greater than 650 psi, a tear resistance greater than about 70 pounds per inch, and a specific heat capacity of about 2 Joules per gram per °C.

* * * * *